United States Patent
Capon

(10) Patent No.: US 11,345,745 B2
(45) Date of Patent: *May 31, 2022

(54) PEPTIDE-HINGE-FREE FLEXIBLE ANTIBODY-LIKE MOLECULE

(71) Applicant: Daniel J. Capon, Hillsborough, CA (US)

(72) Inventor: Daniel J. Capon, Hillsborough, CA (US)

(73) Assignee: BIOMOLECULAR HOLDINGS LLC, Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,641

(22) Filed: Aug. 7, 2017

(65) Prior Publication Data
US 2017/0342142 A1 Nov. 30, 2017

Related U.S. Application Data

(63) Continuation of application No. 14/569,070, filed on Dec. 12, 2014, now Pat. No. 9,725,503, which is a continuation of application No. 14/354,984, filed as application No. PCT/JP2012/061529 on May 1, 2012, now abandoned.

(60) Provisional application No. 61/553,910, filed on Oct. 31, 2011.

(51) Int. Cl.
| | |
|---|---|
| *C07K 16/18* | (2006.01) |
| *C07K 7/08* | (2006.01) |
| *C07K 14/47* | (2006.01) |
| *C07K 7/06* | (2006.01) |

(52) U.S. Cl.
CPC .............. *C07K 16/18* (2013.01); *C07K 7/06* (2013.01); *C07K 7/08* (2013.01); *C07K 14/4711* (2013.01); *C07K 2317/53* (2013.01); *C07K 2319/02* (2013.01); *C07K 2319/30* (2013.01)

(58) Field of Classification Search
CPC ............ C07K 2317/53; C07K 2319/30; C07K 2317/52
See application file for complete search history.

(56) References Cited

U.S. PATENT DOCUMENTS

| | | | | |
|---|---|---|---|---|
| 6,756,480 B2 * | 6/2004 | Kostenuik | ............ | C07K 14/635 530/387.1 |
| 7,833,979 B2 * | 11/2010 | Sullivan | .................. | A61P 19/02 514/9.7 |
| 9,725,503 B2 * | 8/2017 | Capon | ...................... | C07K 7/06 |
| 2006/0269553 A1 * | 11/2006 | Kim | ........................ | C07K 14/56 424/155.1 |
| 2008/0254512 A1 * | 10/2008 | Capon | ...................... | A61P 17/06 435/69.6 |
| 2015/0183858 A1 | 7/2015 | Capon | | |

FOREIGN PATENT DOCUMENTS

| | | | |
|---|---|---|---|
| JP | 07-501451 A | 2/1995 | |
| JP | 10-501701 A | 2/1998 | |
| JP | 2011-526792 A | 10/2011 | |
| JP | 6158090 | 6/2017 | |
| JP | 6352354 | 7/2018 | |
| WO | WO-9902711 A2 * | 1/1999 | ............. A61P 35/02 |
| WO | WO 99/41279 A2 | 8/1999 | |
| WO | WO 2007/108152 A1 | 9/2007 | |
| WO | WO 2013/065343 A1 | 5/2013 | |

OTHER PUBLICATIONS

Capon, et al., "Flexible antibodies with nonprotein hinges", Proc. Jpn. Acad., Ser. B, Nov. 11, 2011, 87 (9), pp. 603-616.
International Search Report issued in connection with PCT International Application No. PCT/JP2012/061529.
Written Opinion of the International Searching Authority issued in connection with PCT International Application No. PCT/JP2012/061529.
Office Action dated Feb. 19, 2016 in connection with related U.S. Appl. No. 14/569,070.
Aug. 18, 2016 Amendment in Response to Feb. 19, 2016 Office Action and Petition for Three-Month Extension of Time filed in connection with related U.S. Appl. No. 14/569,070.
Office Action dated Oct. 6, 2016 in connection with related U.S. Appl. No. 14/569,070.
Feb. 6, 2017 Amendment in Response to Oct. 6, 2016 Final Office Action as a Submission under 37 C.F.R. §1.114 Accompanying a Request for Continued Examination, and Petition for One-Month Extension of Time filed in connection with related U.S. Appl. No. 14/569,070.
Notice of Allowance dated Apr. 3, 2017 in connection with related U.S. Appl. No. 14/569,070.
U.S. Appl. No. 61/553,910, Tanaka.
Oct. 3, 2018 First Office Action issued in connection with Japanese Patent Application No. 2016184967 including English language translation thereof.
Apr. 2, 2019 Response to Oct. 3, 2018 Office Action filed in connection with Japanese Patent Application No. 2016184967 including English language version thereof.
Timeline of events related to the filing of U.S. Appl. No. 61/553,910 and applications claiming priority thereto.

* cited by examiner

*Primary Examiner* — Peter J Reddig
(74) *Attorney, Agent, or Firm* — John P. White

(57) ABSTRACT

The present invention provides an antibody that can bind to targets with greater affinity. A flexible antibody-like molecule having a nonpeptide hinge part comprising: a group having a nonpeptide hinge part represented by a general formula (I): XY-Asp-Lys-Thr-His-Thr (SEQ ID No. 1)—wherein X represents an amino acid or a peptide composed of 2 to 50 amino acid residues, and Y represents for a group having an alkyleneoxide; and an antibody Fc fragment bound to the group having a nonpeptide hinge part.

18 Claims, 14 Drawing Sheets
Specification includes a Sequence Listing.

| | |
|---|---|
| 1 | Fc6 |
| 2 | DKTHT-Fc6 |
| 3 | DAEFRHDSGYEVHHQ-DKTHT-Fc6 |
| 4 | DAEFRHDSGYEVHHQ-PEG$_{12}$-DKTHT-Fc6 |
| 5 | DAEFRHDSGYEVHHQ-PEG$_{24}$-DKTHT-Fc6 |
| 6 | DAEFRHDSGYEVHHQ-PEG$_{36}$-DKTHT-Fc6 |

(SEQ ID NO: 2)      (SEQ ID NO: 1)

Fig.9
A) Aβ-Fc
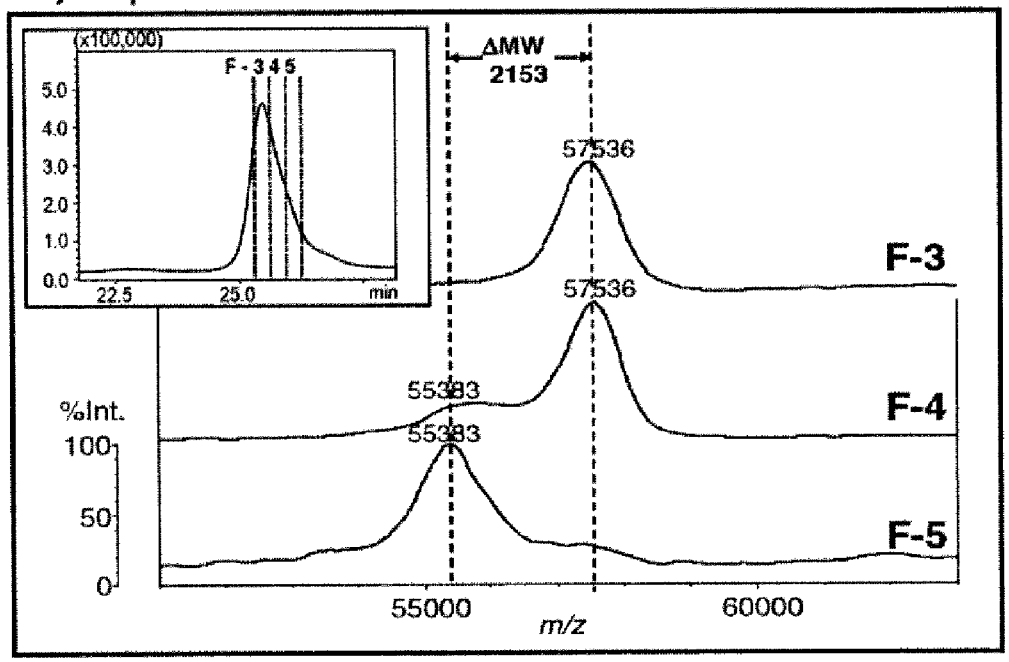
B) Aβ-PEG$_{12}$-Fc
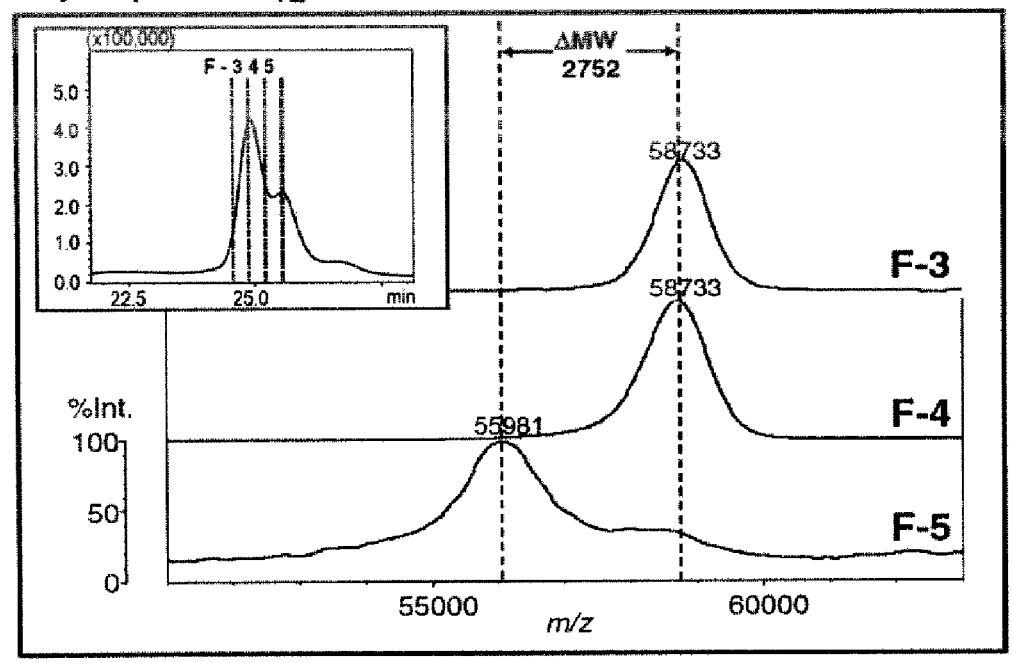

Fig.10
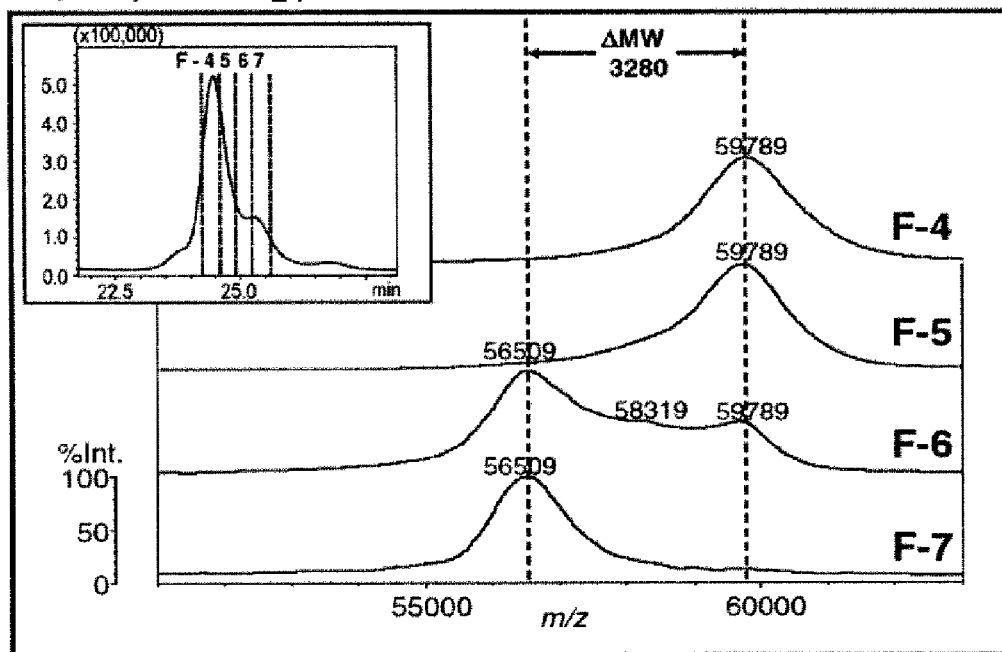
C) Aβ-PEG$_{24}$-Fc
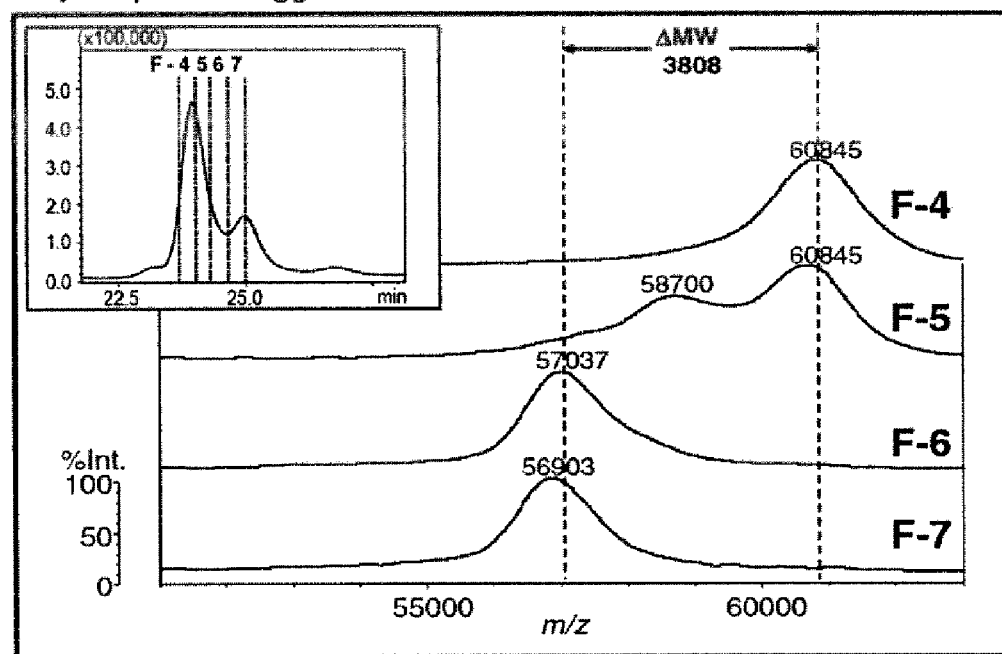
D) Aβ-PEG$_{36}$-Fc

Fig.12
A) DAEFRHDSGYEVHHQ-DKTHT-Fc6 (SEQ ID NO: 2) (SEQ ID NO: 1)
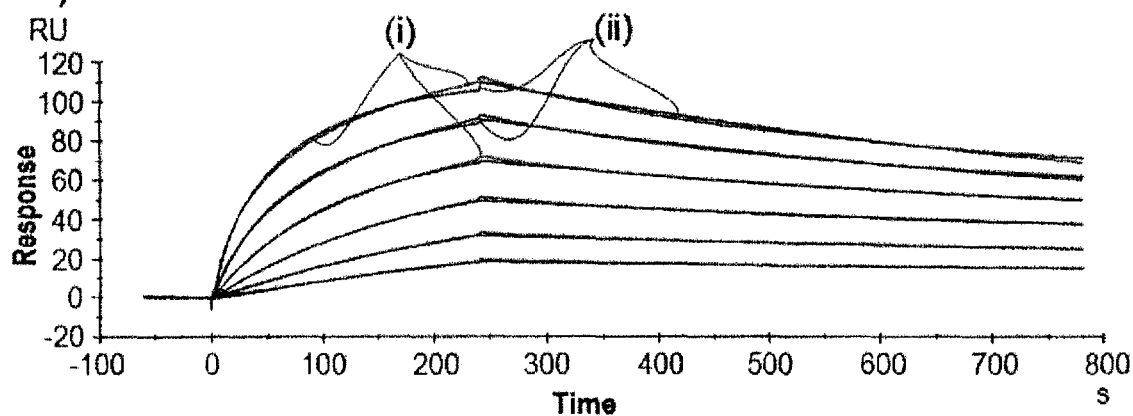
B) DAEFRHDSGYEVHHQ-PEG$_{12}$-DKTHT-Fc6 (SEQ ID NO: 2) (SEQ ID NO: 1)
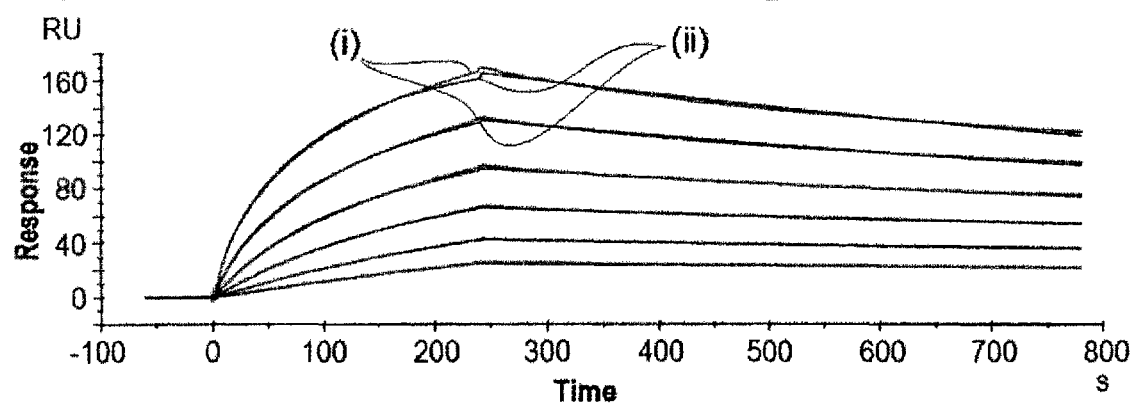

Fig.13
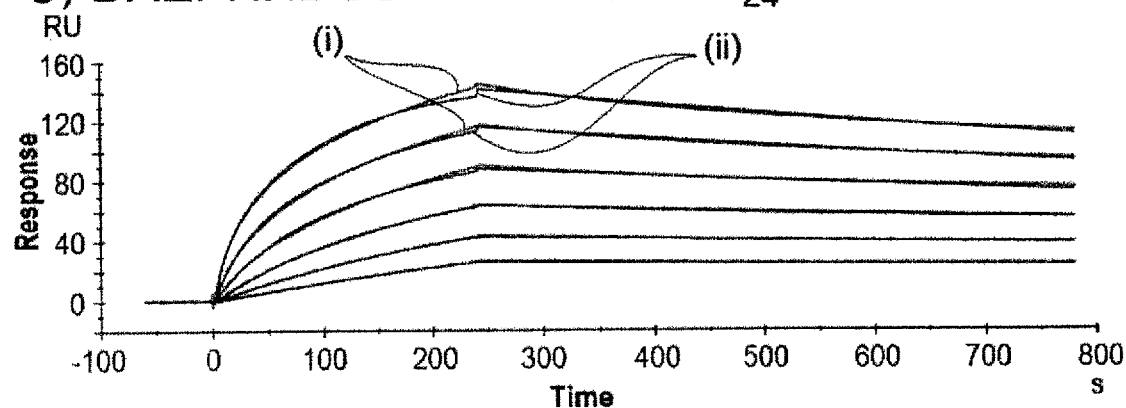
C) DAEFRHDSGYEVHHQ-PEG$_{24}$-DKTHT-Fc6 (SEQ ID NO: 2) (SEQ ID NO: 1)
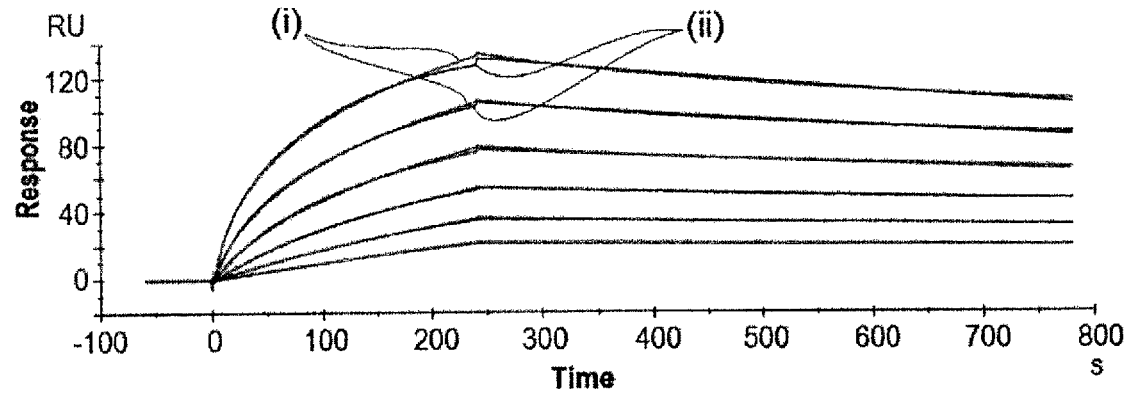
D) DAEFRHDSGYEVHHQ-PEG$_{36}$-DKTHT-Fc6 (SEQ ID NO: 2) (SEQ ID NO: 1)

Fig.14
E) pen-DAEFRHDSGYEVHHQ (SEQ ID NO: 2)
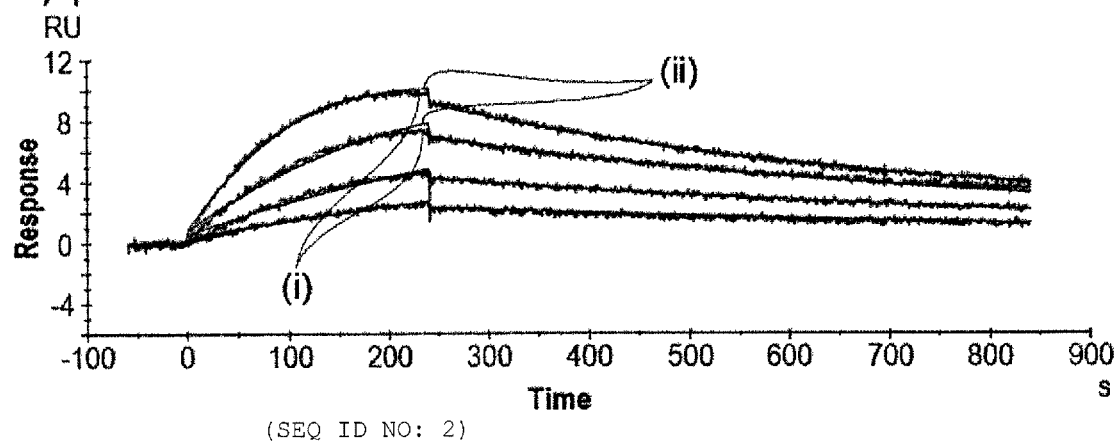
F) DAEFRHDSGYEVHHQ-pra (SEQ ID NO: 2)
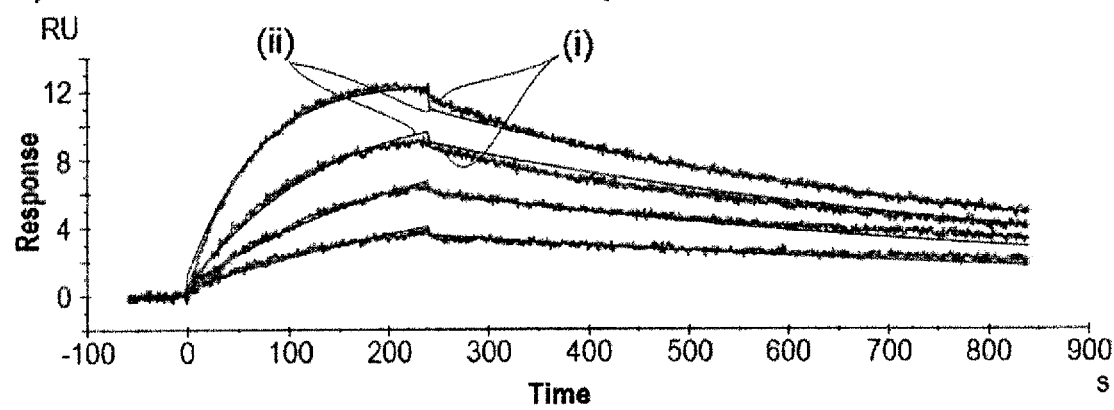

SEQUENCE LISTING

```
<160> NUMBER OF SEQ ID NOS: 10

<210> SEQ ID NO 1
<211> LENGTH: 5
<212> TYPE: PRT
<213> ORGANISM: human

<400> SEQUENCE: 1

Asp Lys Thr His Thr
1               5

<210> SEQ ID NO 2
<211> LENGTH: 15
<212> TYPE: PRT
<213> ORGANISM: human

<400> SEQUENCE: 2

Asp Ala Glu Phe Arg His Asp Ser Gly Tyr Glu Val His His Gln
1               5                   10                  15

<210> SEQ ID NO 3
<211> LENGTH: 5
<212> TYPE: PRT
<213> ORGANISM: human

<400> SEQUENCE: 3

Glu Phe Arg His Asp
1               5

<210> SEQ ID NO 4
<211> LENGTH: 42
<212> TYPE: PRT
<213> ORGANISM: human
```

```
<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
                35                  40

<210> SEQ ID NO 5
<211> LENGTH: 4
<212> TYPE: PRT
<213> ORGANISM: human

<400> SEQUENCE: 5

Cys Pro Pro Cys
1

<210> SEQ ID NO 6
<211> LENGTH: 8
<212> TYPE: PRT
<213> ORGANISM: human

<400> SEQUENCE: 6

Pro Ala Glu Leu Leu Gly Gly Pro
1               5

<210> SEQ ID NO 7
<211> LENGTH: 10
<212> TYPE: PRT
<213> ORGANISM: human

<400> SEQUENCE: 7

Ser Val Phe Leu Phe Pro Pro Lys Pro Lys
1               5                   10

<210> SEQ ID NO 8
<211> LENGTH: 6
<212> TYPE: PRT
<213> ORGANISM: human

<400> SEQUENCE: 8

Cys Asp Lys Thr His Thr
1               5

<210> SEQ ID NO 9
<211> LENGTH: 26
<212> TYPE: PRT
<213> ORGANISM: human

<400> SEQUENCE: 9

Thr His Thr Cys Pro Pro Cys Pro Ala Pro Glu Leu Leu Gly Gly Pro
1               5                   10                  15

Ser Val Phe Leu Phe Pro Pro Lys Pro Lys
                20                  25

<210> SEQ ID NO 10
<211> LENGTH: 8
<212> TYPE: PRT
<213> ORGANISM: human
```

```
<400> SEQUENCE: 10

Asp Ala Glu Phe Arg His Asp Ser
1               5
```

PEPTIDE-HINGE-FREE FLEXIBLE ANTIBODY-LIKE MOLECULE

CROSS REFERENCE TO RELATED APPLICATION

This application is a continuation of U.S. Ser. No. 14/569,070, filed Dec. 12, 2014, issued as U.S. Pat. No. 9,725,503, which is a continuation of U.S. Ser. No. 14/354,984, filed Apr. 29, 2014, now abandoned, which is a § 371 national stage of PCT International Application No. PCT/JP2012/061529, filed May 1, 2012, claiming the benefit of U.S. Provisional Application No. 61/553,910, filed Oct. 31, 2011, the entire contents of each of which are incorporated herein by reference.

REFERENCE TO A SEQUENCE LISTING

This application incorporates-by-reference nucleotide and/or amino acid sequences which are present in the file named "170807_87151-AAA-PCT-US_Substitute_Sequence_Listing _CAE.txt" which is 2.07 kilobytes in size, and which was created Aug. 7, 2017 in the IBM-PC machine format, having an operating system compatibility with MS-Windows, which is contained in the text file filed Aug. 7, 2017 as part of this application.

TECHNICAL FIELD

The present invention relates to an artificial antibody. More specifically, the present invention relates to a flexible antibody-like molecule having a nonpeptide hinge part.

BACKGROUND ART

The essence of an antibody molecule is its Y-shape. By 1940, Pauling envisioned that antibodies have three regions and correctly predicted that the middle part has the same configuration as normal γ-globulin while the two ends have variable configurations that are complementary to the surface of an antigen[1] (Non-Patent Document 1). Porter proved in 1958 that γ-globulin is formed from three globular sections, and demonstrated that these sections could be split apart by papain[2] (Non-Patent Document 2). The sequence of one part (Fc) of these sections was shown to be essentially conserved in all γ-globulins, while the other two sections (Fab) were shown to vary considerably in sequence from molecule to molecule. By 1969, Edelman et al. presented a complete description of the connections between the Fab region and the Fc region[3] (Non-Patent Document 3). Papain cleavage occurs within two heavy chains so that Fab arms, each of which has a light chain bound to the N-terminal portion of the heavy chain by a disulfide, are released from an Fc fragment that is a disulfide-bound dimer composed of the C-terminal half of the heavy chains. All of the cysteines participating in these interchain disulfide bonds are clustered at the very middle of the heavy chain, giving the γ-globulins their Y-shape.

A more dynamic picture of γ-globulin structure has emerged from electron microscopy of antibody-antigen complexes[4],[5] (Non-Patent Documents 4 and 5). In the presence of divalent haptens, antibodies form cyclic dimers, trimers, tetramers, pentamers, and larger structures. Although the Fab part and the Fc part have the appearance of rigid rods, the angle between them varies from zero to 180°, allowing them to bridge antigens at distances up to 120 angstroms. The antibody behaves as if all the three parts were bound by a "hinge part" that is a name now used for a heavy chain region containing interchain disulfides. Despite its small size of just ten amino acids in IgG1, the hinge part displays considerable variation in its configuration. The one available crystal structure of a human IgG1 having a full-length hinge part[6] (Non-Patent Document 6) reveals extreme asymmetry in the placement of the Fab arms, and this reflects differences in their distance and rotational displacement from Fc. Although the hinge parts on adjacent heavy chains are mutually separated by a distance of 18 angstroms or less, the Fab arms diverge at a 148° angle along their major axes and are rotated by 158° along their depth axes.

At the beginning of 1989, Capon et al. reported that the Fab arms of IgG could be replaced with a variety of other proteins including the extracellular domains of CD4, L-selectin, and tumor necrosis factor (TNF) receptor[7] to [14] (Non-Patent Documents 7 to 14). These Y-shaped antibody-like molecules (called immunoadhesins or Fc fusion proteins) are cleaved by papain, like antibodies, into three fragments and have many of the biological properties of IgG including a long plasma half-life, Fc receptor and complement binding, and the ability to cross the placenta. All of them were shown to have therapeutic potential. Specifically, CD4 immunoadhesin prevented HIV-1 infection in chimpanzees, L-selectin immunoadhesin blocked neutrophil influx in mice, and TNF receptor immunoadhesin protected mice against lethal endotoxic shock. Their prolonged half-life in the blood[7] (Non-Patent Document 7) has proven particularly valuable, and it leads to the approval of five therapeutic drugs, i.e., etanercept (TNF receptor), abatacept (CTLA-4), alefacept (LFA-3), rilonacept (IL-1 receptor), and romiplostim (thrombopoietin analog)[15] (Non-Patent Document 15).

PRIOR ART DOCUMENTS

Non-Patent Documents

Non-Patent Document 1: Pauling, L. (1940) A theory of the structure and process of formation of antibodies. J. Am. Chem. Soc. 62, 2643-2657.

Non-Patent Document 2: Porter, R. R. (1958) Separation and isolation of fractions of rabbit gamma-globulin containing the antibody and antigenic combining sites. Nature 182, 670-671.

Non-Patent Document 3: Edelman, G. M., Cunningham, B. A., Gall, W. E., Gottlieb, P. D., Rutishauser, U. and Waxdal, M. J. (1969) The covalent structure of an entire .Gimmunoglobulin molecule. Proc. Natl. Acad. Sci. U.S.A. 63, 78-85.

Non-Patent Document 4: Feinstein, A. and Rowe, A. J. (1965) Molecular mechanism of formation of an antigen-antibody complex. Nature 205, 147-149.

Non-Patent Document 5: Valentine, R. C. and Green, N. M. (1967) Electron microscopy of an antibody hapten complex. J. Mol. Biol. 27, 615-617.

Non-Patent Document 6: Saphire, E. O., Stanfield, R. L., Crispin, M. D., Parren, P. W., Rudd, P. M., Dwek, R. A., Burton, D. R. and Wilson, I. A. (2002) Contrasting IgG structures reveal extreme asymmetry and flexibility. J. Mol. Biol. 319, 9-18.

Non-Patent Document 7: Capon, D. J., Chamow, S. M., Mordenti, J., Marsters, S. A., Gregory, T., Mitsuya, H., Byrn, R. A., Lucas, C., Wurm, F. M., Groopman, J. E., Broder, S. and Smith, D. H. (1989) Designing CD4 immunoadhesins for AIDS therapy. Nature 337, 525-531.

Non-Patent Document 8: Byrn, R. A., Mordenti, J., Lucas, C., Smith, D., Marsters, S. A., Johnson, J. S., Cossum, P., Chamow, S. M., Wurm, F. M., Gregory, T., Groopman, J. E. and Capon, D. J. (1990) Biological properties of a CD4 immunoadhesin. Nature 344, 667-670.

Non-Patent Document 9: Chamow, S. M., Peers, D. H., Byrn, R. A., Mulkerrin, M. G., Harris, R. J., Wang, W. C., Bjorkman, P. J., Capon, D. J. and Ashkenazi, A. (1990) Enzymatic cleavage of a CD4 immunoadhesin generates crystallizable, biologically active Fd-like fragments. Biochemistry 29, 9885-9891.

Non-Patent Document 10: Ward, R. H., Capon, D. J., Jett, C. M., Murthy, K. K., Mordenti, J., Lucas, C., Frie, S. W., Prince, A. M., Green, J. D. and Eichberg, J. W. (1991) Prevention of HIV-1 IIIB infection in chimpanzees by CD4 immunoadhesin. Nature 352, 434-436.

Non-Patent Document 11: Watson, S. R., Imai, Y., Fennie, C., Geoffrey, J. S., Rosen, S. D. and Lasky, L. A. (1990) A homing receptor-IgG chimera as a probe for adhesive ligands of lymph node high endothelial venules. J. Cell Biol. 110, 2221-2229.

Non-Patent Document 12: Watson, S. R., Fennie, C. and Lasky, L. A. (1991) Neutrophil influx into an inflammatory site inhibited by a soluble homing receptor-IgG chimaera. Nature 349, 164-167.

Non-Patent Document 13: Ashkenazi, A., Marsters, S. A., Capon, D. J., Chamow, S. M., Figari, I. S., Pennica, D., Goeddel, D. V., Palladino, M. A. and Smith, D. H. (1991) Protection against endotoxic shock by a tumor necrosis factor receptor immunoadhesin. Proc. Natl. Acad. Sci. U.S.A. 88, 10535-10539.

Non-Patent Document 14: Ashkenazi, A., Capon, D. J. and Ward, R. H. (1993) Immunoadhesins. Int. Rev. Immunol. 10, 219-227.

Non-Patent Document 15: Reichert, J. M. (2011) Antibody-based therapeutics to watch in 2011. MAbs 3, 76-99.

SUMMARY OF THE INVENTION

Problems to be Solved by the Invention

There is a great need for antibodies that can bind to targets with greater affinity.

The above-described approved therapeutic antibodies are directed against targets that are multimeric proteins. This suggests that the therapeutic antibodies could be improved if both arms could grasp a particular target molecule. Unfortunately, this task is not straightforward as the hinge part normally points the Fab arms away from each other. Outwardly pointing arms may have evolved to grasp large disease targets such as bacteria, but inwardly pointing arms would make it easy to grasp smaller targets such as proteins (e.g., TNF) The latter would likely require that the hinge part is not only flexible but also extendible to a distance of at least several nanometers away from Fc (a combination of properties that are found in many types of polymer chains, but are typically lacking in polypeptides[16]).

Means for Solving the Problems

An attractive solution is to create an antibody hinge part that is both flexible and extendible by employing nonprotein chains. Here, the present inventors will describe significant progress towards these goals.

The present inventors have devised a chemical synthesis method based on a native chemical ligation[17] that gives quantitative yields of Fc fusion proteins but is appropriate to a native, biologically active Fc molecule. The present inventors will report a novel chemical synthesis method for producing a symmetroadhesin that is an antibody-like molecule having a nonprotein hinge region that is more flexible and extendible and is capable of two-handed binding.

Using this approach, the present inventors fused a 15 amino acid peptide having the immunodominant epitope of Alzheimer's Aβ(1-42) fibrils[18] to [21] and successfully incorporated nonprotein chains between the Aβ and Fc moieties. That is, a native chemical ligation was performed under mild, non-denaturing conditions to bind a ligand binding domain (Aβ peptide) to an IgG1 Fc dimer via discrete oxyethylene oligomers of various lengths. Two-handed Aβ-Fc fusion proteins were obtained in quantitative yield and shown by surface plasmon resonance to bind to an anti-Aβ antibody with a $K_D$ that is at least two orders of magnitude smaller than a control Aβ peptide.

MALDI-TOF MS, as developed by Tanaka et al.[22],[23], was applied to confirm the structure of the nonprotein chain by virtue of the ionization and desorption of the adjacent protein regions. MALDI-TOF MS analysis confirmed the protein/nonprotein/protein structure of the two-handed molecule, and this demonstrated that complex protein-nonprotein hybrids were detected by desorption/ionization of peptide sequences contained therein. The present inventors anticipate many applications for symmetroadhesins that combine the target specificity of antibodies with the novel physical, chemical, and biological properties of nonprotein hinge part.

The present invention includes the following aspects.

(1) A flexible antibody-like molecule having a nonpeptide hinge part comprising:

a group having a nonpeptide hinge part represented by a general formula (I):

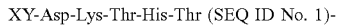

XY-Asp-Lys-Thr-His-Thr (SEQ ID No. 1)- wherein X represents an amino acid or a peptide composed of 2 to 50 amino acid residues, and Y represents for a group having an alkyleneoxide; and an antibody Fc fragment bound to the group having a nonpeptide hinge part.

(2) The flexible antibody-like molecule according to the above (1), wherein the X is an amyloid β.

(3) The flexible antibody-like molecule according to the above (1) or (2), wherein the Y is a polyethyleneglycol group with a polymerization degree of 2 to 50.

(4) The flexible antibody-like molecule according to the above (1), wherein the X is an amyloid β (1-15) Asp-Ala-Glu-Phe-Arg-His-Asp-Ser-Gly-Tyr-Glu-Val-His-His-Gln (SEQ ID No. 2), the Y is a polyethyleneglycol group with a polymerization degree of 12 to 36, the antibody Fc fragment is in a dimer form, and a number of the group having a nonpeptide hinge part is two.

(5) A method for producing a flexible antibody-like molecule having a nonpeptide hinge part, the method comprising:

preparing a thioester containing a nonpeptide hinge part represented by a general formula (II):

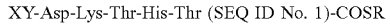

XY-Asp-Lys-Thr-His-Thr (SEQ ID No. 1)-COSR wherein X represents an amino acid or a peptide composed of 2 to 50 amino acid residues, Y represents a group having an alkyleneoxide, COSR represents a thioester group of C-terminal threonine residue of the amino acid sequence Asp-Lys-Thr-His-Thr (SEQ ID No. 1), and R represents an organic group;

preparing a peptide containing an antibody Fc fragment, the peptide having an antibody Fc fragment and an N-terminal cysteine residue; and subjecting the thioester containing a nonpeptide hinge part and the peptide containing an antibody Fc fragment to a native chemical ligation to obtain an antibody-like molecule which comprises a group containing a nonpeptide hinge part represented by XY-Asp-Lys-Thr-His-Thr (SEQ ID No. 1)- and an antibody Fc fragment bound to the group containing a nonpeptide hinge part via the cysteine residue.

Effects of the Invention

The present invention can provide an antibody-like molecule that can bind to a target with higher affinity (specifically, with a smaller dissociation constant $K_D$).

The molecule having at least two hands provided by the present inventors binds to a target with exceptional affinity, and therefore such an improved antibody holds great promise for future development of antibody therapeutics.

BRIEF DESCRIPTION OF THE DRAWINGS

FIG. 9 illustrates the MS spectra of two main peaks of SEC chromatograms of the Aβ-PEG$_x$-Fc fusion proteins: (A) Aβ-Fc; and (B) Aβ-PEG$_{12}$-Fc, wherein the insets indicate fractions selected from their respective chromatograms for MS analysis (the same applies to FIG. 10).

FIG. 10 illustrates the MS spectra of two main peaks of SEC chromatograms of the Aβ-PEG$_x$-Fc fusion proteins: (C) Aβ-PEG$_{24}$-Fc; and (D) Aβ-PEG$_{36}$-Fc.

FIG. 12 illustrates the results of surface plasmon resonance (SPR) analysis of binding of anti-AβmAb (6E10) by the Aβ-PEG$_x$-Fc fusion proteins ((A) Aβ-Fc, (B) Aβ-PEG$_{12}$-Fc), wherein actual binding curve traces are indicated by (i) and binding curve fits are indicated by (ii) (the same applies to FIGS. 13 and 14).

FIG. 13 illustrates the results of surface plasmon resonance (SPR) analysis of binding of anti-AβmAb (6E10) by the Aβ-PEG$_x$-Fc fusion proteins ((C) Aβ-PEG$_{24}$-Fc, (D) Aβ-PEG$_{36}$-Fc).

FIG. 14 illustrates the results of surface plasmon resonance (SPR) analysis of binding of anti-AβmAb (6E10) by Aβ$_{1-15}$ peptides ((E) pen-(Aβ$_{1-15}$), (F) (Aβ$_{1-15}$)-pra).

MODES FOR CARRYING OUT THE INVENTION

Figure 1:
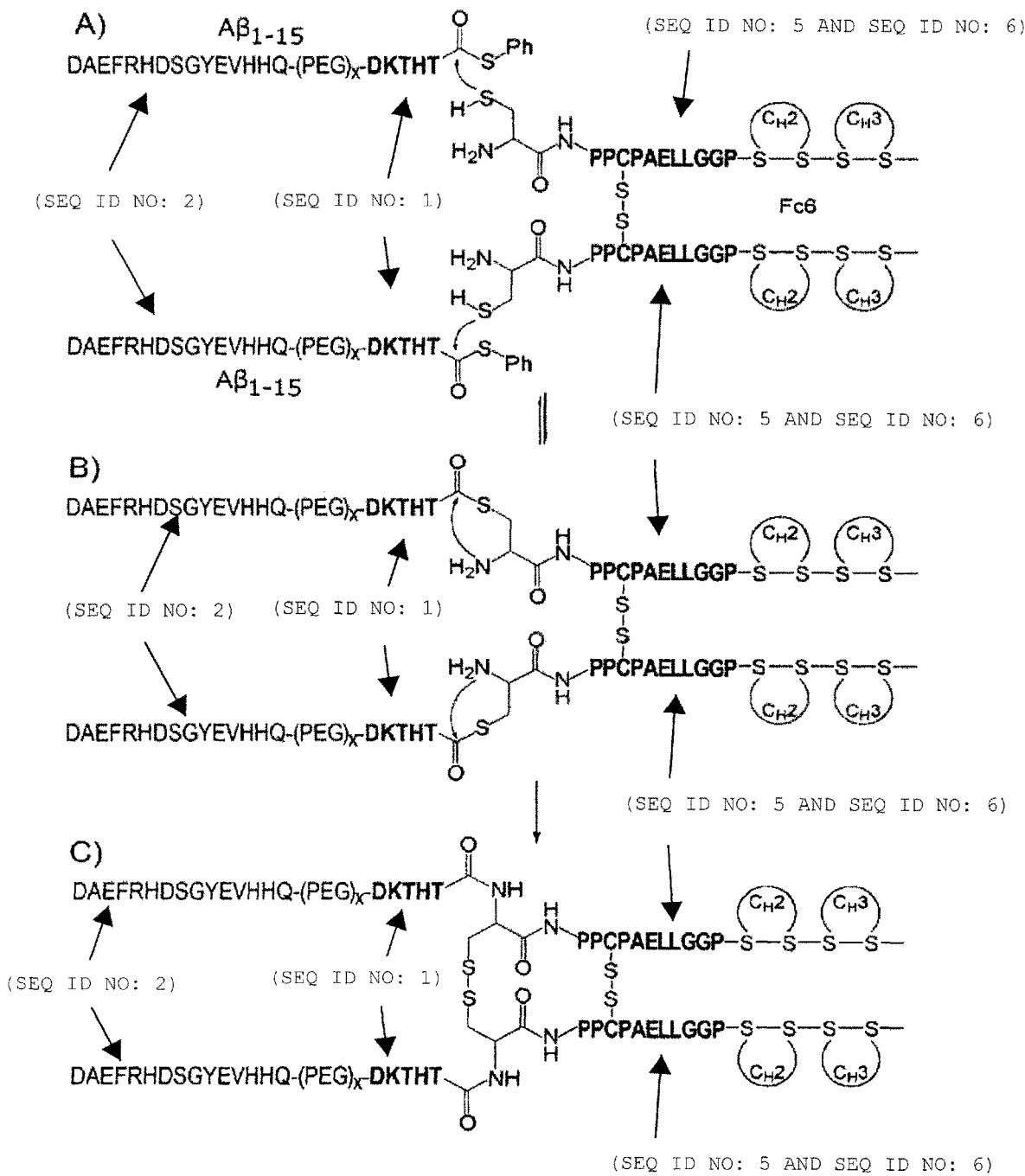
FIG. 1 illustrates the chemical semisynthesis of an Aβ-PEG$_x$-Fc fusion protein, and shows the following steps: (A) reversible formation of an S-acyl intermediate by transthioesterification; (B) the S-acyl intermediate undergoing spontaneous S- to N-acyl migration; and (C) irreversible formation of peptide bond via a five-membered intermediate, wherein the IgG1 hinge region is indicated by boldface.

A flexible antibody-like molecule having a nonpeptide hinge part according to the present invention comprises a molecular recognition system-forming substance X, an alkyleneoxide group-containing group Y bound to the molecular recognition system-forming substance X, an antibody hinge region-forming sequence bound to the alkyleneoxide-containing group, and an antibody Fc fragment bound to the antibody hinge region-forming sequence. The term "binding" includes direct binding and indirect binding.

The molecular recognition system-forming substance X may be one of a guest substance (target molecule) and a host substance (molecular recognition substance) that are generally capable of interacting by non-covalent bond with each other, and specifically, may be an amino acid, a peptide, or a polypeptide (including a protein). Particularly, the molecular recognition system-forming substance X may be an amino acid, a peptide composed of 2 to 50 amino acid residues, or a polypeptide.

Examples of the guest substance include various physiological active substances, but the guest substance is preferably a disease-related substance. A specific example of the guest substance includes amyloid β (peptide chain comprising all or part of a well-known sequence of amyloid β). More specifically, the guest substance is a peptide chain having at least the sequence of amyloid β (3-7) EFRHD (SEQ ID No. 3) that is the epitope of amyloid β. Examples of the peptide chain include a peptide chain having the sequence of amyloid β (3-7), a peptide chain having the sequence of amyloid β (1-15), DAEFRHDSGYEVHHQ (SEQ ID No. 2), a peptide chain having the sequence of amyloid β (1-42), DAEFRHDSGYEVHHQKLVFFAEDGSNKGAIIGLMVGGVVIA (SEQ ID No. 4), and the like.

The host substance may be a substance that is capable of molecular recognition of the target molecule (which may be either a biological molecule or a non-biological molecule).

Examples of the host substance include an antibody Fab fragment, an aptamer, and the like.

Molecular recognition means that the molecular recognition site of a molecular recognition substance recognizes and interacts by non-covalent bond with the epitope of a specific target molecule. For example, molecular recognition may be affinity specific binding at an association rate constant ka (unit: 1/Ms) of at least $10^3$ or $10^4$, for example, $10^3$ to $10^5$ or $10^4$ to $10^5$.

The alkyleneoxide-containing group Y is a bivalent group and may be, for example, a group containing an alkyleneoxide with 2 to 6 carbon atoms. More specifically, the alkyleneoxide in the alkyleneoxide-containing group is ethyleneoxide or propyleneoxide. The alkyleneoxide-containing group is preferably a polyalkyleneoxide-containing group. Therefore, the alkyleneoxide-containing group is preferably a polyalkyleneglycol group formed by polymerization of alkyleneglycol with 2 to 6 carbon atoms (e.g., polymerization degree of 2 to 50). For example, the polyalkyleneglycol group may be selected from the group consisting of a polyethyleneglycol group (a group formed by polymerization of ethyleneglycol) and a polypropyleneglycol group (a group formed by polymerization of 1,2-propanediol or 1,3-propanediol).

Particularly, in the present invention, an ethyleneglycol group or a polyethyleneglycol group with a polymerization degree of 2 to 50, preferably 12 to 36 may be selected.

The alkyleneoxide-containing group Y imparts flexibility, or flexibility and extendibility to the hinge region of the antibody-like molecule according to the present invention.

Examples of the antibody include IgG1, IgG2, IgG3, IgG4, and the like. The antibody may be one derived from any animal, but is particularly one derived from a human. Further, the antibody may be modified in terms of genetic engineering.

Examples of the antibody hinge region-forming sequence include an antibody upper hinge region-forming sequence $Z_U$, an antibody core hinge region-forming sequence $Z_C$, and an antibody lower hinge region-forming sequence $Z_L$, and the antibody-like molecule according to the present invention may contain all these sequences. Generally, a core hinge region is a region that is adjacent to the C-terminal side of an upper hinge region and the N-terminal side of a lower hinge region in the hinge region of an antibody, and has at least two cysteine residues forming interchain disulfide bridges between heavy chains.

Each of the hinge region-forming sequences is part or all of the sequence of each of the hinge regions. Far example, the upper hinge region-forming sequence $Z_U$ may be part of the sequence of the upper hinge region, for example, a short sequence composed of, for example, 3 to 5 amino acid residues. For example, the upper hinge region-forming sequence $Z_U$ is part of the sequence of the IgG1 upper hinge region, DKTHT (SEQ ID No. 1). Further in this case, it is preferred that no cysteine residue is bound to the N-terminal of the sequence DKTHT in the antibody-like molecule according to the present invention.

The core hinge region-forming sequence $Z_C$ has at least two cysteine residues forming interchain disulfide bridges between heavy chains, and the N terminal-side cysteine residue of the two cysteine residues preferably corresponds to the N-terminal amino acid residue of the core hinge region-forming sequence $Z_C$. One example of the core hinge region-forming sequence $Z_C$ is CPPC (SEQ ID No. 5) that is the sequence of the IgG1 core hinge region.

One example of the antibody lower hinge region-forming sequence $Z_L$ is PAELLGGP (SEQ ID No. 6) that is the sequence of the IgG1 antibody lower hinge region.

The antibody Fc fragment is a polypeptide forming part or all of an antibody Fc region. Specifically, the antibody Fc fragment may have the second heavy chain constant region (CH2) and the third heavy chain constant region (CH3). As one example, the antibody Fc fragment may comprise a sequence containing of SVFLFPPKPK (SEQ ID No. 7) as at least part. The Fc fragment may be in the form of a dimer or a larger multimer (e.g., up to a decamer).

When the Fc fragment is in the form of a dimer, the antibody-like molecule according to the present invention has two nonpeptide hinge part-containing groups ($XYZ_U$-groups) each containing the molecular recognition system-forming substance X, the alkyleneoxide-containing group Y, and the antibody upper hinge region-forming sequence $Z_U$. The antibody-like molecule having such a structure may be referred to as a two-handed antibody-like molecule. Similarly, when the Fc fragment in the antibody-like molecule according to the present invention is in the form of a dimer or a larger multimer, the antibody-like molecule may have two or more nonpeptide hinge part-containing groups ($XYZ_U$-groups) and therefore may form two or more-handed antibody-like molecule.

A counterpart substance of X, which forms a molecular recognition system in which the antibody-like molecule according to the present invention can be involved, is determined by those skilled in the art based on the properties of X.

The counterpart substance may be a monomeric molecule, a dimer or a larger multimer of molecules, or an aggregate of molecules.

The counterpart substance may be either a biological substance or a non-biological substance.

The counterpart substance may be a low molecular-weight molecule (e.g., molecular weight of 80,000 or less, or 30,000 or less). For example, the counterpart substance maybe a low molecular-weight protein such as cytokine.

Flexibility offered by the presence of the alkyleneoxide-containing group Y makes it possible for at least one of the two or more hands of the antibody-like molecule according to the present invention to always bind with a counterpart substance. This makes it easy to maintain a state where the counterpart substance is grasped by the hand(s). That is, the counterpart substance is less likely to be dissociated. Specifically, the association rate constant ka (unit: 1/Ms) of each hand is as described above and is equal to that in a case where the molecular recognition system-forming substance X is a single molecule, but the dissociation rate constant kd (unit: 1/s) is smaller than that in such a case as described above. Therefore, the dissociation constant $K_D$ (unit: M) is smaller than that in such a case as described above, and may be, for example, at most $10^{-9}$, $10^{-10}$, $10^{-11}$, or $10^{-12}$, for example, $10^{-13}$ to $10^{-9}$.

The antibody-like molecule according to the present invention may be used in any application utilizing a molecular recognition system. Examples of such an application include in-vitro diagnostic agents, molecular target drugs, ELISA (Enzyme-Linked ImmunoSorbent Assay) reagents, probes for molecular imaging [PET (positron emission tomography), optical imaging], and the like. Those skilled in the art can select an appropriate molecular recognition system-forming substance X depending on the intended use of the antibody-like molecule. If necessary, the antibody-like molecule may further contain a functional group (signal group, etc.).

The antibody-like molecule according to the present invention is produced in the following manner.

A nonpeptide hinge part-containing thioester ($XYZ_U$-COSR) containing a molecular recognition system-forming substance X, an alkyleneoxide-containing group Y, and an antibody upper hinge region-forming sequence $Z_U$ is prepared. COSR represents for a thioester group (derivable from a carboxyl group) of the C-terminal amino acid residue of the antibody upper hinge region-forming sequence $Z_U$, and R represents an organic group (e.g., a linear or branched alkyl group with 1 to 18 carbon atoms, an aryl group with 6 to 18 carbon atoms, an aralkyl group as a combination thereof).

The molecular recognition system-forming substance X may be either a biological substance or a non-biological substance, and may be obtained by any method which is well-known to those skilled in the art such as isolation from a natural product, organic chemical synthesis, biochemical production, or semisynthesis.

The biochemical production includes enzymatic synthesis/decomposition and genetic engineering synthesis (host cells may be either prokaryotic cells such as bacteria, or eukaryotic cells such as yeasts or animal cells) (the same applies to the following other components).

The antibody upper hinge region-forming sequence $Z_U$ may be either a biological sequence or a non-biological sequence, and may be obtained by any method which is well-known to those skilled in the art such as isolation from a natural product, organic chemical synthesis, biochemical production, or semisynthesis.

A method which is well-known to those skilled in the art can be performed for obtaining the molecular recognition system-forming substance X and the antibody upper hinge region-forming sequence $Z_U$ in a state where these components are linked together via the alkyleneoxide-containing group Y. The thioester group can be appropriately derived from the C-terminal carboxyl group of the antibody upper hinge region-forming sequence by those skilled in the art.

On the other hand, an antibody Fc fragment-containing peptide having an antibody Fc fragment and an N-terminal cysteine residue is prepared. The antibody Fc fragment-containing peptide may have an amino acid residue or a peptide chain L between the N-terminal cysteine residue and the Fc fragment [represented by Cys-L-Fc (L is an amino acid residue or a peptide chain)]. The antibody Fc fragment-containing peptide preferably has at least one another cysteine residue between the cysteine residue and the antibody Fc fragment [e.g., represented by Cys-$L_1$-Cys-$L_2$-Fc ($L_1$ and $L_2$ are an amino acid residue or a peptide chain)]. Specifically, it is preferred that the antibody Fc fragment-containing peptide contains an antibody core hinge region-forming sequence $Z_C$, and the N-terminal cysteine residue corresponds to an N-terminal cysteine residue of the antibody core hinge region-forming sequence $Z_C$. Further, it is also preferred that the above-described at least one another cysteine residue is also contained in the antibody core hinge region-forming sequence $Z_C$ [e.g., represented by Cys-$L_1$-Cys-$L_2$-Fc (Cys-$L_1$-Cys is the antibody core hinge region-forming sequence $Z_C$)]. The antibody Fc fragment-containing peptide may further contain an antibody lower hinge region-forming sequence $Z_L$ [e.g., represented by Cys-$L_1$-Cys-$L_2$-Fc ($L_2$ is the antibody lower hinge region-forming sequence $Z_L$)].

The antibody Fc fragment-containing peptide can be obtained by a peptide production method which is well-known to those skilled in the art. Therefore, the antibody Fc fragment-containing peptide may be obtained by any method which is well-known to those skilled in the art such as isolation from a natural product, organic chemical synthesis, biochemical production, semisynthesis, and the like, or a combination of two or more of them.

The nonpeptide hinge part-containing thioester ($XYZ_U$-COSR) and the antibody Fc fragment-containing peptide (e.g., Cys-L-Fc) are brought into contact with each other so that a negative chemical ligation reaction occurs. The reaction can be performed by incubation in a buffer solution under non-heating conditions (room temperature) for 6 to 16 hours. As a result, an antibody-like molecule having the $XYZ_U$-group and the antibody Fc fragment, to which the $XYZ_U$-group is bound via the cysteine residue (e.g., $XYZ_U$-Cys-L-Fc), is obtained.

FIG. 1 illustrates the mechanism of the native chemical ligation with reference to one example of the present invention. FIG. 1 illustrates a case where the nonpeptide hinge part-containing thioester contains amyloid β (1-15) DAE-FRHDSGYEVHHQ (SEQ ID No. 2) as the molecular recognition system-forming substance X, polyethyleneglycol with a polymerization degree of x $(PEG)_x$ as the alkyleneoxide-containing group Y, and DKTHT (SEQ ID No. 1) as the antibody upper hinge region-forming sequence $Z_U$; and the antibody Fc fragment-containing peptide is a peptide having CPPC (SEQ ID No. 5) as the antibody core hinge region-forming sequence $Z_C$ and PAELLGGP (SEQ ID No. 6) as the antibody lower hinge region-forming sequence $Z_L$.

In the native chemical ligation, an S-acyl intermediate is reversibly formed by transthioesterification (FIG. 1A), the S-acyl intermediate undergoes spontaneous S- to N-acyl migration (FIG. 1B), and a peptide bond is irreversibly formed via a five-membered ring intermediate (FIG. 1C).

EXAMPLES

[Materials and Methods]
[Human IgG1 Fc Protein]

A recombinant Fc protein (called Fc6) was expressed in Chinese hamster ovary (CHO) cells and purified by Protein A affinity chromatography. A DNA expression vector was designed that directs the expression of a chimeric protein containing a human sonic hedgehog homolog (SHH) signal sequence fused to a human IgG1 heavy chain hinge region beginning at a [226]CPPC core hinge sequence (heavy chain residues are numbered according to the Eu format[3]; residue [226]Cys corresponds to Cys239 in kobat & Wu format)[24]. The sequence of this vector (pCDNA3-SHH-IgG1-Fc11) is described in Capon, D. J. (Nov. 20, 2008) World Patent Cooperation Treaty, Publication No. WO/2008/140477. Following secretion and cleavage of the SHH signal sequence, the resulting mature Fc6 polypeptide has a predicted length of 222 residues. Production of an Fc6 protein was executed by transient expression in CHO-DG44 cells adapted to a serum-free suspension medium. Transient transfections were performed using polyethyleneimine as a transfection agent by forming a complex with DNA under high density conditions as previously described[25]. Seed train cultures were maintained in 50 tubes of TubeSpin (registered trademark) bioreactor and scaled up in volume in order to generate sufficient biomass for transfection. Transfections were carried out in culture fluids of 0.5 Liter to 1 Liter. Cultures at this scale were maintained in 2-Liter or 5-Liter Schott-bottles with a ventilated cap. The bottles were shaken at 180 rpm in a Kuhner incubator shaker with humidification and $CO_2$ control at 5 vol %. The cell culture fluid was recovered after 10 days, centrifuged, and sterile-filtered prior to purification. The culture supernatant was applied to a column packed with rProtein A Fast Flow (GE Healthcare Bio-Sciences AB, Uppsala, Sweden) pre-equilibrated with Dulbecco's phosphate buffered saline (PBS) without Ca or Mg salts (UCSF Cell Culture Facility, San Francisco, Calif.). The column was extensively washed with PBS, and the Fc6 protein was eluted with 0.1 M glycine buffer, pH 2.7. Fractions were collected into tubes containing 0.05 v/v, 1.0 M Tris-HCl, pH 9.0 (giving a final pH of 7.5), pooled, dialyzed against PBS, and stored at 4° C. prior to use.

[Peptides]

All synthetic peptides used in this study are shown in Table 1.

In Table 1, amino acid sequences (Sequence) are indicated by boldface. Thioester in Peptides 1, 4, and 5 is derived from thiophenol, and thioester in Peptides 2 and 3 is derived from benzyl mercaptan. Mr stands for a relative molecular mass, and MH$^+$ stands for a monoisotopic mass (measured value).

TABLE 1

| Peptide | No. | Mr (Da) | MH$^+$ | Sequence |
|---|---|---|---|---|
| Aβ-DKTHT | 1 | 2515.6 | 2516.68 | DAEFRHDSGYEVHHQ-DKTHT-*thioester* |
| Aβ-PEG$_{12}$-DKTHT | 2 | 3115.6 | 3115.64 | DAEFRHDSGYEVHHQ-*PEG$_{12}$*-DKTHT-*thioester* |
| Aβ-PEG$_{24}$-DKTHT | 3 | 3629.7 | 3629.67 | DAEFRHDSGYEVHHQ-*PEG$_{24}$*-DKTHT-*thioester* |
| Aβ-PEG$_{36}$-DKTHT | 4 | 4158.2 | 4158.40 | DAEFRHDSGYEVHHQ-*PEG$_{36}$*-DKTHT-*thioester* |
| DKTHT | 5 | 776.8 | 776.60 | *Azidoacetyl*-DKTHT-*thioester* |
| pen-Aβ | 6 | 1921.0 | 1921.94 | *pentynoyl*-DAEFRHDSGYEVHHQ-*NH$_2$* |
| Aβ-pra | 7 | 1905.9 | 1906.56 | DAEFRHDSGYEVHHQ-*propargylglycine-NH$_2$* |

DKTHT = SEQ ID NO: 1
DAEFRHDSGYHVHHQ = SEQ ID NO: 2

All the peptides shown in Table 1 were synthesized by an Fmoc/t-butyl solid-phase strategy on a 2-chlorotrityl chloride resin preloaded with Fmoc-Thr(tBu)-OH. Amino acid derivatives were obtained from CPC Scientific (Sunnyvale, Calif.), Fmoc-PEG$_x$-OH derivatives were purchased from Quanta BioDesign (Powell, Ohio), and 2-(1H-benzotriazole-1-yl)-1,1,3,3-tetramethyluronium hexafluorophosphate (HBTU), dichloromethane (DCM), trichloroacetic acid (TFA), N,N'-diisopropylcarbodiimide (DIC), 1-hydroxybenzotriazole (HOBt), N,N'-diisopropylethylamine (DIEA) and triisopropylsilane (TIS) were purchased from Sigma (St. Louis, Mo.). The standard HBTU activation was employed for peptide elongation. Peptides 2-4 required the insertion of Fmoc-PEG$_x$-OH (x=12, 24, and 36, respectively). As a final step in the peptide elongation, the terminal α-Fmoc (9-fluorenylmethoxycarbonyl) protecting group was converted to Boc (tert-butoxycarbonyl). The peptide resin was washed with DCM and cleaved with 1% TFA/DCM (volumetric basis) to yield a fully-protected peptide having a free carboxylic acid on the C-terminus. The crude protected peptide was treated with DIC/HOBt/DIEA and either thiophenol (Peptides 1, 2, 5) or benzyl mercaptan (Peptides 3, 4) in DCM overnight to form a thioester of the peptide. After concentration, the crude protected peptide thioester was precipitated by multiple triturations with cold ether, followed by centrifugation. Deprotection was carried out by treatment of the crude protected product with 95:2.5:2.5 TFA/TIS/H$_2$O (volume ratio) at room temperature for 2 hours. After precipitation with ice-cold ether, the deprotected peptide thioester was purified by preparative RP-HPLC in a H$_2$O-acetonitrile (0.1 vol % TFA) system to obtain a final product with a purity of 91-95% and a desired MS.

[Chemical Semisynthesis of Symmetroadhesins]

2-(N-morpholino)ethanesulfonic acid (MES) was purchased from Acros (Morris Plains, N.J.), tris(2-carboxyethyl)phosphine (TCEP) was purchased from Pierce (Rockford, Ill.), and 4-mercaptophenylacetic acid (MPAA) was purchased from Sigma-Aldrich (St. Louis, Mo.). Reactions contained pH 6.5, 50 mM MES buffer, 0.8 mM TCEP, 10 mM MPAA, 5 mg/ml of the peptide thioester, and 1 mg/ml of the Fc6 protein. Following incubation at room temperature for 15 hours, reactions were adjusted to pH 7.0 with 0.05 v/v of 1 M Tris-HCl, pH 9.0 and purified on HiTrap Protein A HP columns purchased from GE Healthcare (Piscataway, N.J.). The reaction products were analyzed by SDS polyacrylamide gel electrophoresis (SDS-PAGE) under reducing conditions using NuPAGE (registered trademark) Novex Bis-Tris Midi Gels (10%) purchased from Invitrogen (Carlsbad, Calif.). Proteins were visualized using Silver Stain Plus or Coomassie Brilliant Blue R-250 purchased from Bio-Rad (Hercules, Calif.).

[In-Gel Tryptic Digestion of Proteins]

HPLC-grade acetonitrile (ACN) and trifluoroacetic acid (TPA) were purchased from Wako Pure Chemical Industries (Osaka, Japan). Ammonium bicarbonate (NH$_4$HCO$_3$), dithiotreitol (DTT), and iodoacetamide (IAA) were purchased from Nacalai Tesque (Kyoto, Japan). Sequence grade trypsin was purchased from Promega (Madison, Wis.). Protein bands from the gel were excised and destained with 300 μl of a solution containing 50% v/v ACN in an aqueous 50 mM NH$_4$HCO$_3$ solution at 4° C. for 45 minutes. The gel pieces were dehydrated in 150 μl of 100% ACN at room temperature for 10 minutes and then dried using Speed Vac (registered trademark) for 30 minutes. A solution having a volume of 100 μl, which contained 10 mM OTT in an aqueous 50 mM NH$_4$HCO$_3$ solution, was added to the dried gels to reduce sulfide bonds at 37° C. for 1 hour. After the solution was removed, the proteins were alkylated in 100 μl of a solution containing 55 mM IAA in an aqueous 50 mM NH$_4$HCO$_3$ solution at room temperature for 1 hour under the dark. Afterward, the gel pieces were washed with 150 μl of an aqueous 50 mM NH$_4$HCO$_3$ solution and then dehydrated in 150 μl of 100% ACN. This step was repeated 2 times. The gel pieces were then dried in a vacuum centrifuge for 30 minutes. The dried gels were rehydrated with 2 μl of a solution containing 50 ng/μl of trypsin in an aqueous 50 mM NH$_4$HCO$_3$ solution, and incubated at room temperature for 5 minutes. Then, 18 μl of ultrapure water was further added, and the proteins were digested at 37° C. overnight. After digestion, 40 μl of an aqueous 50% v/v ACN solution containing 0.1% v/v TFA was added to the digestion mixtures, and the gel pieces were sonicated for 15 minutes. The supernatant was collected into new 0.5 ml tubes.

[MALDI-TOF MS Analysis]

MALDI mass spectra were obtained using AXIMA performance MALDI-TOF mass spectrometer (Shimadzu/KRATOS, Manchester, UK) equipped with a 337 nm nitrogen laser in the positive ion reflectron mode and the linear mode. α-Cyano-4-hydroxy-cinnamic acid (CHCA) and sinapinic acid (SA) were obtained from LaserBio Labs (Sophia-Antipolis Cedex, France). As MALDI matrices, CHCA was used for trypsin-digested proteins and SA was used for SEC-separated proteins. A matrix solution was prepared by dissolving 5 mg of the matrix compound in 0.5 ml of an aqueous 50% v/v ACN solution containing 0.1% v/v TFA. A sample solution (0.5 µl) was mixed with an equivalent amount of the matrix solution on a target plate and then dried at room temperature for MALDI-TOF MS analysis. The m/z values were calibrated using, as external standard, 2 pmol of each of [Angiotensin I+H$^+$] (m/z 1296.7), [Angiotensin II+H$^+$] (m/z 1046.5), [[Glu1]-Fibrinopeptide B+H$^+$] (m/z 1570.7), [N-acetyl-resin substrate tetradecapeptide I+H$^+$] (m/z 1800.9), [ACTH fragment 1-17+H$^+$] (m/z 2093.1) and [ACTH fragment 18-39+H$^+$] (m/z 2464.2), and 3 pmol of [ACTH fragment 7-38+H$^+$] (m/z 3656.9), 7.5 pmol of [Bovine serum albumin+H$^+$] (m/z 66430.09 (average)), and [Aldolase+H$^+$] (m/z 39212.28 (average)).

[Size Exclusion Chromatography (SEC)]

SEC was carried out using a Prominence HPLC System (Shimadzu Corp, Kyoto, Japan) or an AKTA Avant FPLC System (GE Healthcare, Piscataway, N.J.), and similar results were obtained. TSKgel columns were purchased from TOSOH Bioscience (Tokyo, Japan). A mobile phase, a flow rate, a column temperature, and a detection wavelength used were 50 mM sodium phosphate, pH 7.4 and 300 mM NaCl, 0.35 mL/minute, 25° C., and 214/280 nm, respectively. All four Aβ-PEG$_x$-Fc symmetroadhhesins (x=0, 12, 24, and 36) were analyzed side-by-side in each experiment. In order to analyze the efficiency of synthesis of two-handed molecules, 5 µL of each of reaction products purified with Protein A was applied to a TSKgel SuperSW 3000 [4.6 mm I.D.×30 cm L] column. The ratio of molecular species was calculated from the area under each peak. In order to confirm the subunit structures of two-handed and one-handed molecules by SDS-PAGE, the reaction products purified with Protein A were first concentrated 10-fold using 0.5 ml Amicon Ultracel-3K centrifugal filters (Millipore, Cork, IR); 50 µl of each concentrate was then applied to four TSKgel columns coupled in series (two G2000SW$_{XL}$ and two G3000SW$_{XL}$ [7.8 mm I.D.×30 cm L] columns). Fractions were then analyzed using NuPAGE (registered trademark) Novex Bis-Tris Midi Gels (4-12%) under reducing conditions. For the determination of the molecular weight of the two major chemical species observed by SEC, 50 µL of each reaction product purified with Protein A was applied to a TSKgel G3000SW$_{XL}$ [7.8 mm I.D.×30 cm L] column. Peak fractions were analyzed by MALDI TOF MS analysis in the linear mode.

[Surface Plasmon Resonance (SPR)]

SPR tests were carried out using a Biacore T100 instrument (Biacore AB, Uppsala, Sweden). A ligand, biotin-labeled 6E10 monoclonal antibody (Covance, Princeton, N.J.), was immobilized at a concentration of 10 mg/ml in PBS onto a CAP sensor chip, Series S, using a Biotin CAPture Kit (GE Healthcare, Piscataway, N.J.). The sensor chip was loaded with a streptavidin capture reagent and regenerated according to the manufacturer's instruction, including an additional regeneration step using 0.25 MNaOH in 30% acetonitrile. Binding of Aβ symmetroadhesins and Aβ peptides was carried out at 25° C. in 10 mM Hepes buffer, pH 7,4, 150 mM NaCl, 3 mM EDTA, and 0.005 vol % Tween-20. Data was evaluated using Biacore T100 Evaluation Software, version 2.0.3.

[Results]

[Quantitative Synthesis of Symmetroadhesins]

A strategy of the present inventors for chemical semisynthesis of Aβ symmetroadhesin is shown in FIG. 1.

A native chemical ligation was carried out using the recombinant Fc protein (Fc6) engineered to have cysteine residues at both N-termini. The present inventors developed mildly reducing, non-denaturing conditions that favor a stable Fc dimer and maintain the sulfhydryl groups of the N-terminal cysteines in a reduced state, allowing the Fc6 molecule to readily react with C-terminal thioesters. Nucleophilic acyl substitution involving both the N-terminal sulfhydryls of the Fc6 molecule as nucleophiles (FIG. 1A) leads to a thioester-linked intermediate having two Aβ thioesters (FIG. 1B). Subsequent nucleophilic attack by both the Fc6 N-terminal amino groups followed by intramolecular rearrangement results in irreversible peptide bond Carnation between Fc6 and two Aβ peptides (FIG. 1C).

In order to obtain the Fc6 protein, the present inventors employed a recombinant DNA construct placed a signal sequence placed adjacent to a cysteine residue normally found in the hinge region. The IgG1 hinge region contains three cysteine residues, i.e., $^{220}$Cys the upper hinge region (CDKTHT (SEQ ID No. 8)) which usually participates in the disulfide bond between the heavy chain and the light chain; and $^{226}$Cys and $^{229}$Cys in the core hinge region (CPPC (SEQ ID No. 5)) which are sometimes present in the interchain disulfide bonds between two heavy chains. The present inventors selected $^{226}$Cys over $^{220}$Cys as the N-terminus for the Fc molecules of the present inventors. The reason for this is that molecules having $^{220}$Cys at their N-terminus (Fc3) were less easily reduced as judged by thiol-sepharose binding experiments (data not shown). In addition, $^{226}$Cys was selected over $^{229}$Cys as the N-terminus. The reason for this is that $^{226}$Cys has a greater potential to stabilize symmetroadhesins, as suggested by the crystallographic structures of a human IgG1, and it shows that the $^{226}$Cys residues are clearly covalently bound while the $^{229}$Cys residues are visibly separated[17].

Figure 2:
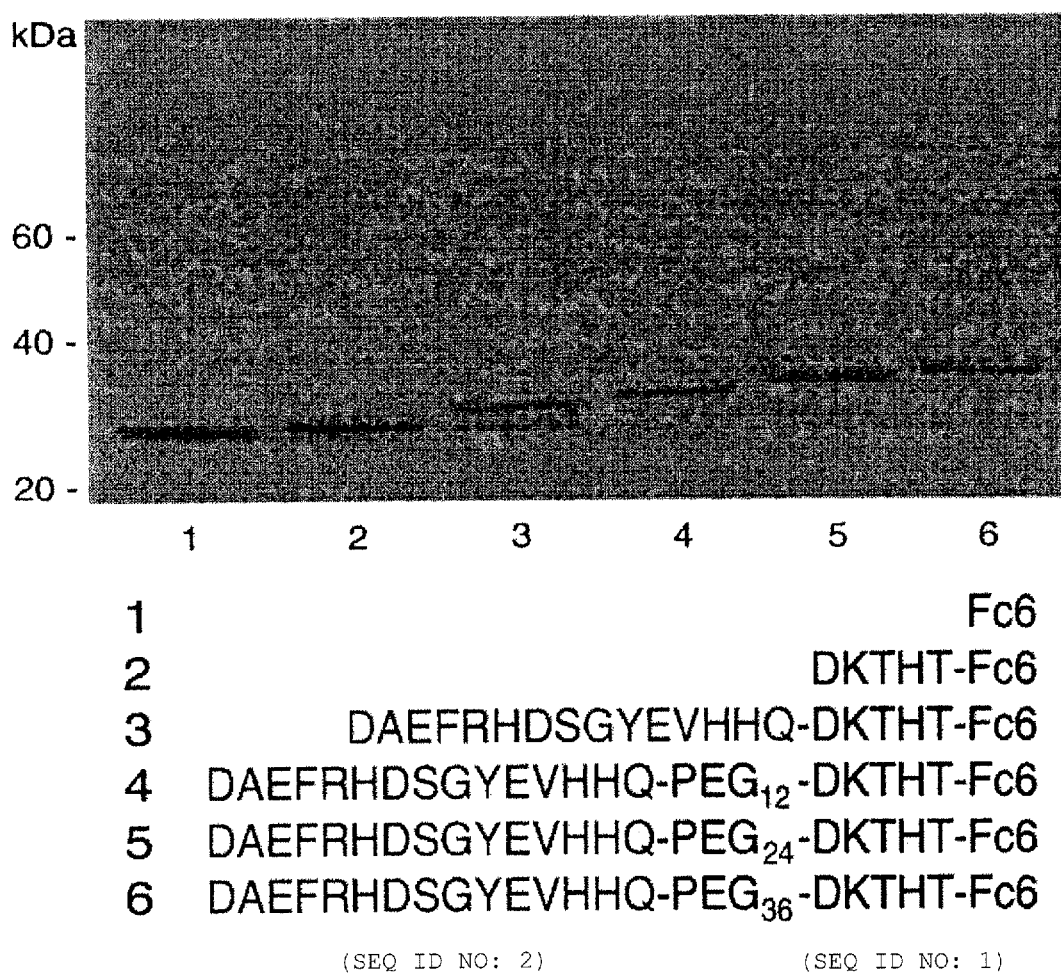
FIG. 2 illustrates the SDS-PAGE analysis of an unreacted Fc6 protein and chemically-synthesized fusion proteins: (1) Fc6; (2) Aβ-Fc; (3) Aβ-PEG$_{12}$-Fc; (4) Aβ-PEG$_{24}$-Fc; and (5) Aβ-PEG$_{36}$-Fc.
Figure 3:
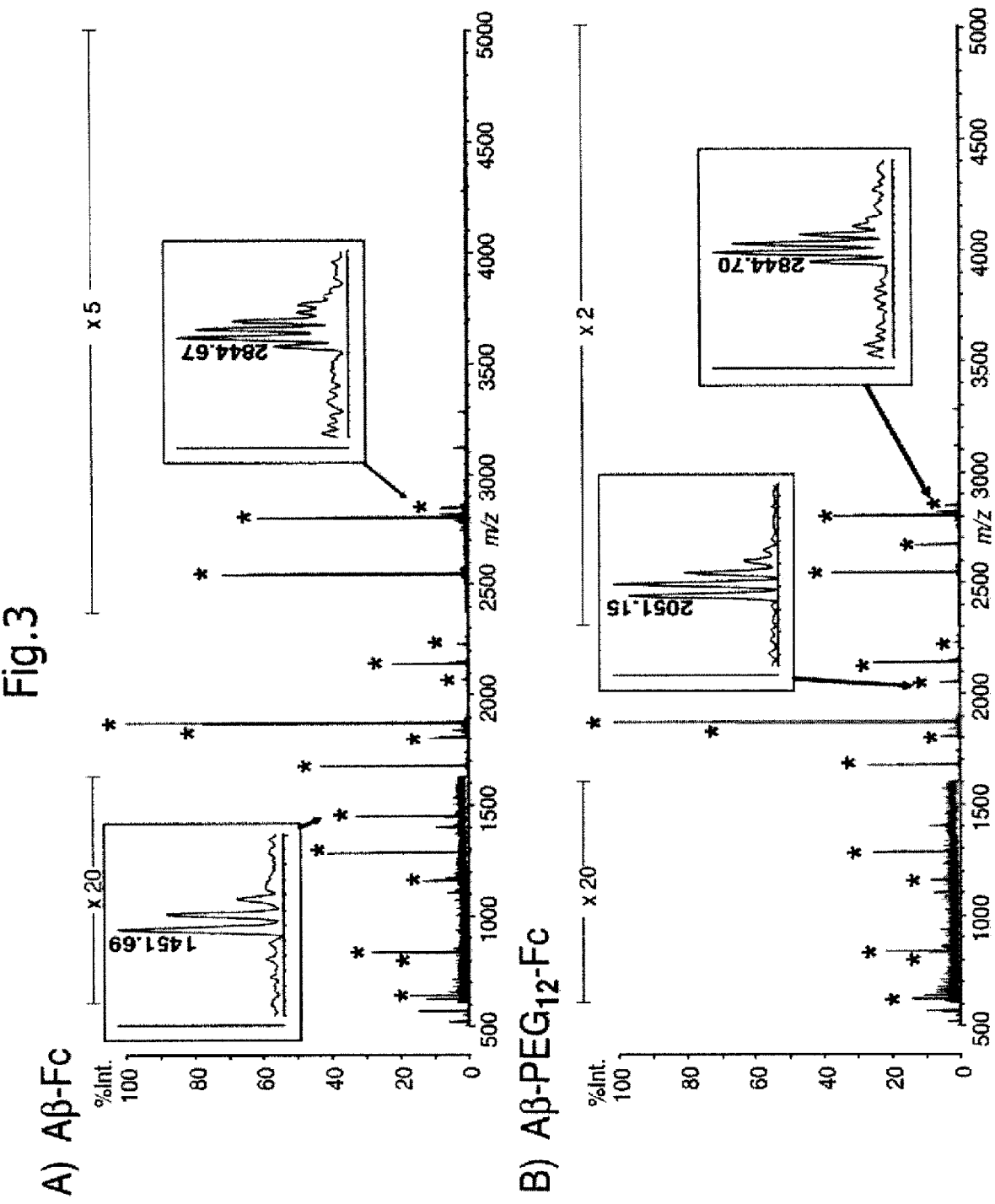
FIG. 3 illustrates the MS spectra of tryptic peptides of the Aβ-PEG$_x$-Fc fusion proteins: (A) Aβ-Fc; and (B) Aβ-PEG$_{12}$-Fc, wherein the asterisks (*) indicate peaks derived from the fusion proteins and the insets indicate Aβ-PEG$_x$-DK and THT-Fc6 fragments.
Figure 4:
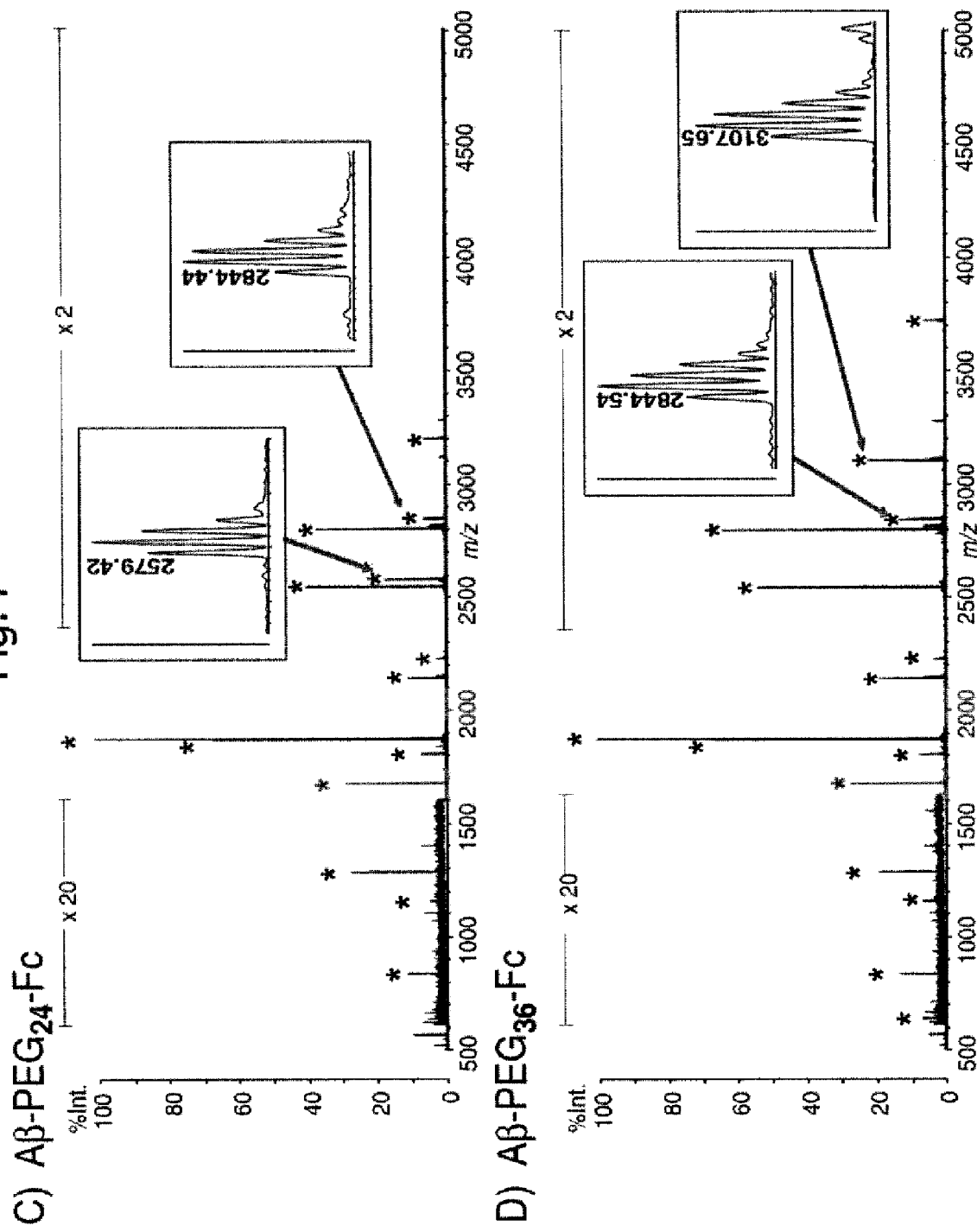
FIG. 4 illustrates the MS spectra of tryptic peptides of the Aβ-PEG$_x$-Fc fusion proteins: (C) Aβ-PEG$_{24}$-Fc; and (D) Aβ-PEG$_{36}$-Fc, wherein the asterisks (*) indicate peaks derived from the fusion proteins and the insets indicate Aβ-PEG$_x$-DK and THT-Fc6 fragments.

The signal sequence of the sonic hedgehog homolog (SHH) was chosen for the secretion and processing of the Fc protein since its own mature polypeptide has an N-terminal cysteine. The pCDNA3-SHH-IgG1-Fc11 construct efficiently directed the synthesis of the Fc6 protein following the transient transfection of Chinese hamster ovary (CHO) cells. FIG. 2 shows that the Fc6 product obtained by the affinity purification of the transfected CHO cell supernatants has an apparent molecular weight of 27,000 daltons on SDS-PAGE under reducing conditions (lane 1). The Fc6 protein was well expressed in transient transfections and reached levels exceeding 0.8 g/L, and was found to quantitatively bind and elute from Protein A affinity resins.

The ability of Fc6 to react with five different C-terminal thioesters (listed in Table 1) was investigated. All the five thioesters contain a portion of the upper hinge region (DKTHT (SEQ ID No. 1)) at their C-terminus. Four of the five thioesters also contain 15 amino acid sequence (DAEFRHDSGYEVHHQ (SEQ ID No. 2)) derived from a human Aβ protein bound at C-terminus to the N-terminus of the upper hinge region. In addition, three of the Aβ-containing thioesters incorporated a nonpeptide chain between the Aβ sequence and the upper hinge sequence. The nonpeptide portions in these peptides were composed of oxyethylene oligomer (PEG) of a chain length of 12, 24, or 36, respectively.

FIG. 2 shows that Fc6 reacted quantitatively with all the five thioesters, so that a ladder of products of increasing size was yielded on SDS-PAGE under reducing conditions (lanes 2-6). Similar to the 15 amino acid residue Aβ sequence, the addition of the PEG$_{12}$ oligomer gave a size increase on SDS-PAGE (compare lanes 2-4 in FIG. 2). This suggests that a single amino acid residue and a single oxyethylene monomer unit make similar contributions to contour length, while being consistent with the comparable lengths of their transconformations (approximately 3.5 to 4 angstroms)[16]. The addition of $PEG_{24}$ and PEG36 gave further size increases over $PEG_{12}$, and the increases were consistent (compare lanes 3-6 in FIG. 2).

Since the present inventors produced Fc6 as a native, folded protein by secretion in mammalian cells, it was critically important to avoid the use of chaotropic agents and strong reducing conditions typically employed in other native chemical ligation studies[17]. Nevertheless, mild reducing conditions were essential. The reason for this is that, otherwise, the Fc6 protein was found to be essentially unreactive with thioesters (data not shown). The quantitative yields of symmetroadhesins (>90%) were readily obtained as seen in FIG. 2 by combining a non-thiol reducing agent such as tris(2-carboxyethyl) phosphine with a thiol reducing agent such as 4-mercaptophenylacetic acid[26].

[Primary Structure Analysis of Symmetroadhesins]

Figure 5:
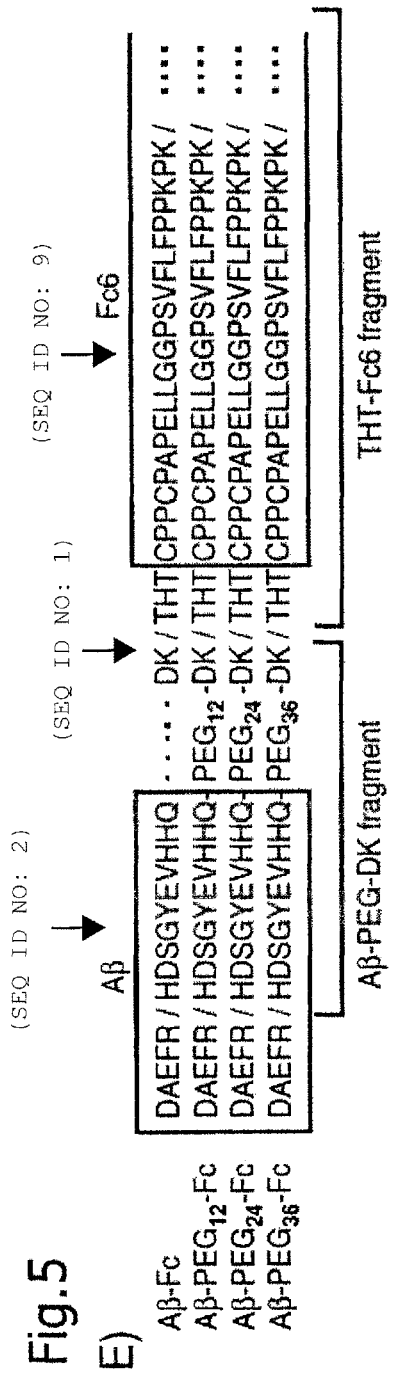
FIG. 5 illustrates the predicted sequence of a ligation site showing the site of tryptic cleavage (E) and the theoretical m/z values of tryptic fragments derived from the ligation site (F).

In order to confirm the exact nature of the chemical linkage between the Aβ sequence and Fc6, the present inventors analyzed the monomer structures of the four Aβ symmetroadhesins by mass spectrometry. The Aβ-Fc, Aβ-$PEG_{12}$-Fc, Aβ-$PEG_{24}$-Fc, and Aβ-$PEG_{36}$-Fc symmetroadhesin reaction products were purified by SDS-PAGE and characterized using in-gel tryptic digestion. Peaks detected by MALDI-TOF MS were fit to theoretical peptides predicted for symmetroadhesins, respectively, so that a sequence coverage between 78.9-81.8% was obtained (FIGS. 3A, 3B, 4C, and 4D). This sequence coverage was sufficient to uniquely identify each of the symmetroadhesins. The present inventors focused analysis on two sequences, i.e., an Aβ-$PEG_x$-DK fragment which should be different in all the four symmetroadhesins; and a THT-Fc6 fragment which represents the chemical ligation site and should be identical in all the four symmetroadhesins (FIG. 5E). The theoretical m/z values for these five predicted sequences are shown in FIG. 5F. The observed MS spectra revealed peaks at m/z values that are in excellent agreement with all four unique fragments (Aβ-DK, Aβ-$PEG_{12}$-DK, Aβ-$PEG_{24}$-DK, Aβ-$PEG_{36}$-DK) as well as the common ligation site fragment (THTCPPCPA-PELLGGPSVFLFPPKPK (SEQ ID No. 9)).

[Subunit Molecular Structure of Symmetroadhesins]

The Aβ symmetroadhesin reaction products were expected to have a dimeric structure similar to that of the parent Fc6 molecule. In addition, when taking into consideration the small amount (<10%) of apparently unreacted substance Fc6 observed in all the four reactions (FIG. 2, lanes 3-6), each of the reaction products maybe a mixture of homodimers having two Aβ "hands", heterodimers having one Aβ "hand", and unreacted Fc6 homodimers. Accordingly, size exclusion chromatography (SEC) was used in order to investigate the subunit molecular structures of the four Aβ symmetroadhesins. The Aβ-Fc, Aβ-$PEG_{12}$-Fc, Aβ-$PEG_{24}$-Fc and Aβ-$PEG_{36}$-Fc reaction products were purified from unreacted thioester by Protein A affinity chromatography, and then analyzed by SEC under native, non-reducing conditions (50 mM sodium phosphate, pH 7.4, 300 mM NaCl). FIGS. 6A, 6B, 7A, and 7B show that all the four symmetroadhesin reaction products exhibited two main peaks. The sizes of these two main peaks increased in the order Aβ-Fc<Aβ-$PEG_{12}$-Fc<Aβ-$PEG_{24}$-Fc<Aβ-$PEG_{36}$-Fc. Furthermore, the size separation between the two main peaks that were observed for a predetermined symmetroadhesin reaction product increased in the same relative order. In addition, all the four symmetroadhesin reaction products exhibited a smaller minor peak at 24.4 minutes having a size expected for the unreacted Fc6 dimer (No Aβ hand). These observation results, when summarized, suggested that the larger and smaller main peaks represent the predicted "two-handed" and "one-handed" symmetroadhesins, respectively.

TABLE 2

| Reaction | Two-handed | One-handed | No Aβ hand | HMW |
|---|---|---|---|---|
| Aβ-Fc | 72.7% | 24.6% | 2.5% | 0.2% |
| Aβ-$PEG_{12}$-Fc | 66.1% | 29.5% | 4.4% | ND |
| Aβ-$PEG_{24}$-Fc | 74.6% | 19.8% | 2.8% | 2.8% |
| Aβ-$PEG_{36}$-Fc | 70.9% | 24.1% | 2.6% | 2.4% |

Table 2 shows Aβ-$PEG_x$-Fc symmetroadhesin product ratios determined by size exclusion chromatography (SEC). The ratios for each of the four reaction (Reaction) products shown in FIGS. 3 and 4 were calculated directly from the area of each peak. HMW represents a molecular species having a higher molecular weight, and ND represents not detected.

As shown in Table 2, the two-handed symmetroadhesin candidate was a major product observed in each of the four reactions (66-74%). Finally, three of the reaction products also exhibited a minor higher molecular weight (HMW) peak (FIGS. 6A, 7C, and 7D). As for the two main peaks, the size of this peak increased along with the length of the oxyethylene oligomer.

In order to confirm the predicted subunit structures of the two-handed and one-handed symmetroadhesins, preparative SEC was carried out under the native, non-reducing conditions (FIG. 8A) and the resulting fractions were analyzed by SDS-PAGE under reducing conditions (FIGS. 8B to 8E). In each of the four symmetroadhesin reactions, the candidate peak for the two-handed symmetroadhesin was composed almost exclusively of the expected Aβ-$PEG_x$-Fc product (x=0, 12, 24, 36), and accordingly its homodimeric structure was confirmed. Similarly, the candidate peak for the one-handed symmetroadhesin was composed of a 1:1 ratio of the expected Aβ-$PEG_x$-Fc product and the apparently unreacted Fc6, and accordingly its heterodimeric structure was confirmed.

In order to establish the exact molecular relationship between the two-handed symmetroadhesin and the one-handed symmetroadhesin, the two main peaks observed on analytical size exclusion chromatograms were analyzed by MALDI-TOF MS in the linear mode (FIGS. 9A, 9B, 10C, and 10D).

TABLE 3

| | MW (observed)[1] | | | MW (theoretical) | |
| | | | | Aβ- | Aβ- |
| Reaction | Two-Handed | One-Handed | ΔMW$^2$ | -PEGx--DKTHT | -PEGx--DKT |
|---|---|---|---|---|---|
| Aβ-Fc | 57,536 | 55,383 | 2,153 | 2,390 | 2,152 |
| Aβ-$PEG_{12}$-Fc | 58,733 | 55,981 | 2,752 | 2,989 | 2,751 |
| Aβ-$PEG_{24}$-Fc | 59,789 | 56,509 | 3,280 | 3,518 | 3,280 |
| Aβ-$PEG_{36}$-Fc | 60,845 | 57,037 | 3,808 | 4,046 | 3,808 |

Figure 6:
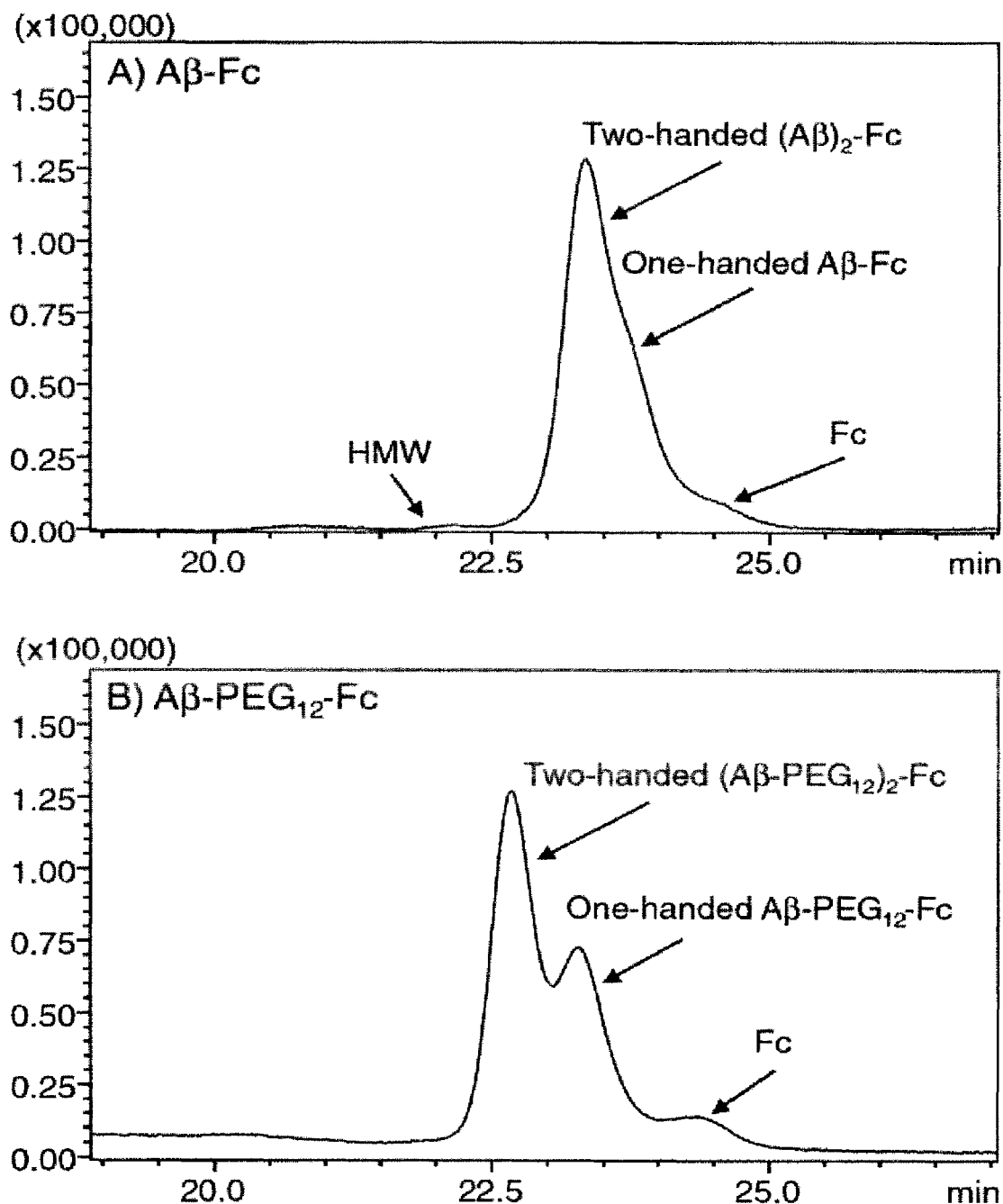
FIG. 6 illustrates the SEC of the Aβ-PEG$_x$-Fc fusion proteins; (A) Aβ-Fc; and (B) Aβ-PEG$_{12}$-Fc, wherein the arrows indicate the positions of main peaks corresponding to an Fc dimer having two Aβ$_{1-15}$ hands, an Fc dimer having one Aβ$_{1-15}$ hand, and an Fc dimer having no Aβ$_{1-15}$ hands, and HMW indicates a molecular species having a higher molecular weight (the same applies to FIG. 7).
Figure 7:
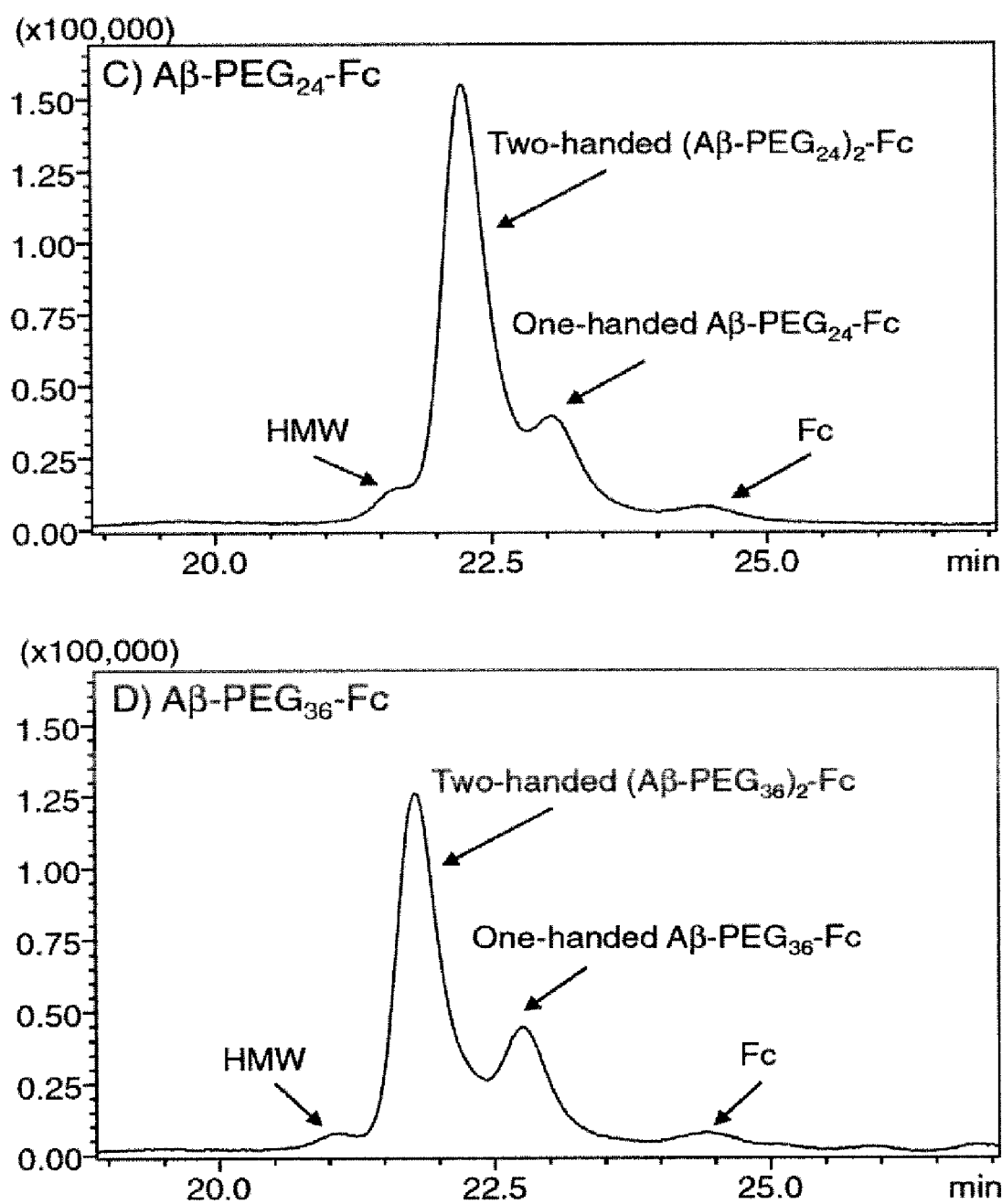
FIG. 7 illustrates the SEC of the Aβ-PEG$_x$-Fc fusion proteins: (C) Aβ-PEG$_{24}$-Fc; and (D) Aβ-PEG$_{36}$-Fc.
Figure 8:
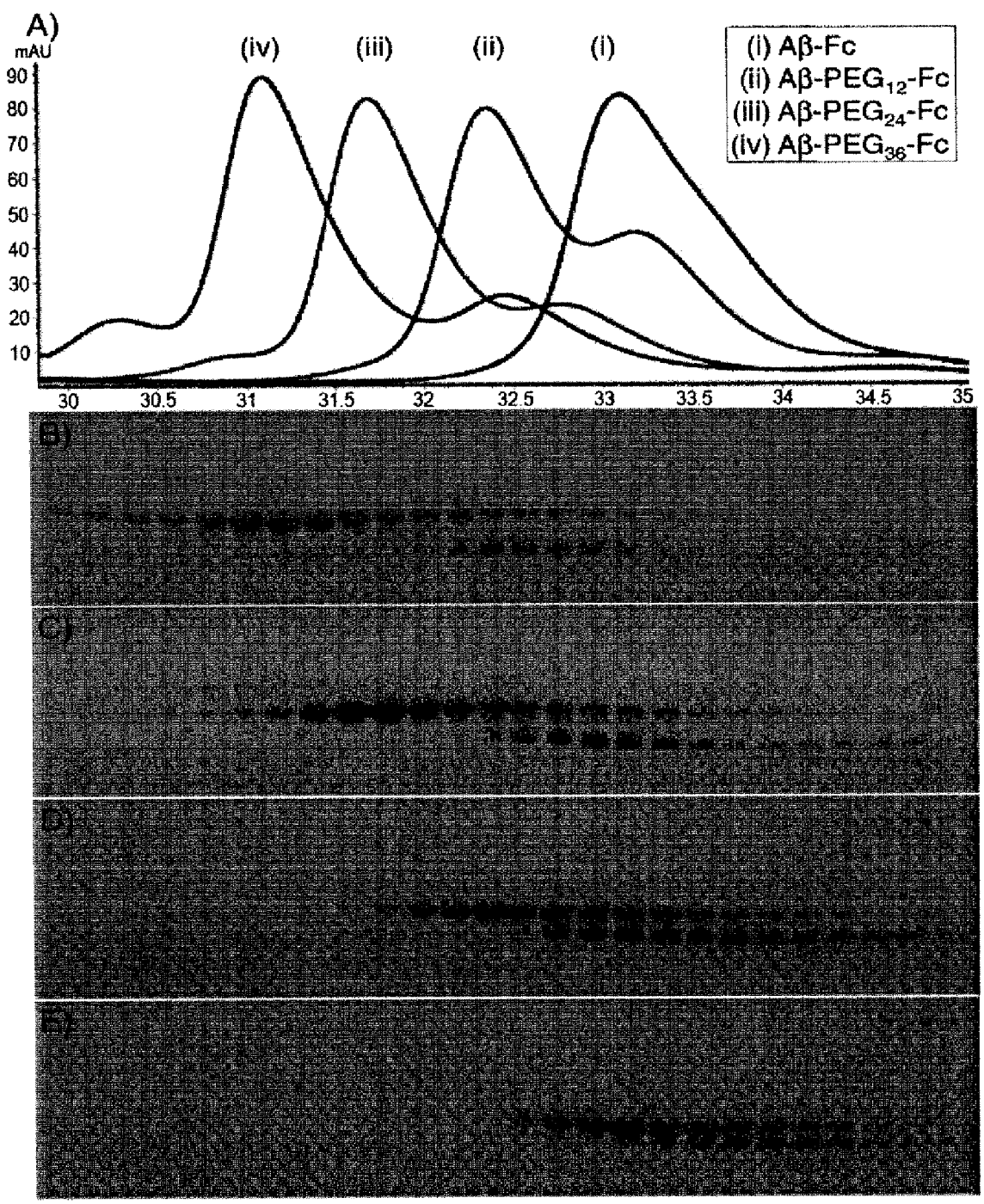
FIG. 8 illustrates the SDS-PAGE analysis of SEC chromatograms of the four Aβ-PEG$_x$-Fc fusion proteins, wherein (A) is the superposition of four chromatograms obtained by injecting equal amounts of the proteins; and (B) to (E) are gel analysis of chromatogram fractions of (B) Aβ-Fc, (C) Aβ-PEG$_{12}$-Fc, (D) Aβ-PEG$_{24}$-Fc, and (E) Aβ-PEG$_{36}$-Fc.

In Table 3, MW (observed)[1] represents the molecular weight of each of the two-handed and one-handed products in each of the four reactions (Reaction) shown in FIGS. 6 and 7, and ΔMW$^2$ represents the difference in molecular weight between the two-handed and one-handed products in each of the reactions (Reaction).

The results shown in Table 3 led to the surprising finding that the difference in molecular weight (ΔMW) between the Aβ-PEG$_x$-Fc reaction product and the apparently "unreacted" Fc6 was consistently approximately 238 daltons greater than the difference expected. For all the four Aβ symmetroadhesins, the observed ΔMW corresponds to the contained the 15 amino acid Aβ sequence. No binding was observed at all with Fc6 or the DKTHT-Fc6 symmetroadhesin (FIG. 2, lane 2), and accordingly it was confirmed that binding was specific for the Aβ sequence.

The binding of 6E10 by the Aβ symmetroadhesins was qualitatively and quantitatively different from that of the Aβ peptides (FIGS. 12 to 14).

TABLE 4

|  | ka2 (1/Ms) | kd2 (1/s) | KD2 (M) | Rmax2 | ka1 (1/Ms) | kd1 (1/s) | KD1 (M) | Rmax1 | Chi$^2$ |
|---|---|---|---|---|---|---|---|---|---|
| Aβ Symmetroadhesin |  |  |  |  |  |  |  |  |  |
| DAEFRHDSGYEVHHQ-DKTHT-Fc6 | 6.119E+04 | 4.742E-05 | 7.749E-10 | 34.9 | 1.010E+04 | 1.414E-03 | 1.401E-07 | 91.5 | 0.96 |
| DAEFRHDSGYEVHHQ-PEG$_{12}$-DKTHT-Fc6 | 7.858E+04 | 4.127E-08 | 5.251E-13 | 37.4 | 8.865E+03 | 8.290E-04 | 9.350E-08 | 155.5 | 0.98 |
| DAEFRHDSGYEVHHQ-PEG$_{24}$-DKTHT-Fc6 | 7.965E+04 | 4.747E-07 | 5.960E-12 | 40 | 9.592E+03 | 6.728E-04 | 7.014E-08 | 119 | 1.1 |
| DAEFRHDSGYEVHHQ-PEG$_{36}$-DKTHT-Fc6 | 8.347E+04 | 4.429E-06 | 5.306E-11 | 29.7 | 9.080E+03 | 5.695E-04 | 6.272E-08 | 119.9 | 0.72 |
| Aβ Peptide |  |  |  |  |  |  |  |  |  |
| pentynoyl-DAEFRHDSGYEVHHQ-NH$_2$ |  |  |  |  | 1.055E+05 | 2.114E-03 | 2.003E-08 | 10.4 | 0.039 |
| DAEFRHDSGYEVHHQ-propargylglycine-NH$_2$ |  |  |  |  | 9.531E+04 | 1.601E-03 | 1.679E-08 | 12.2 | 0.075 |

Figure 11:
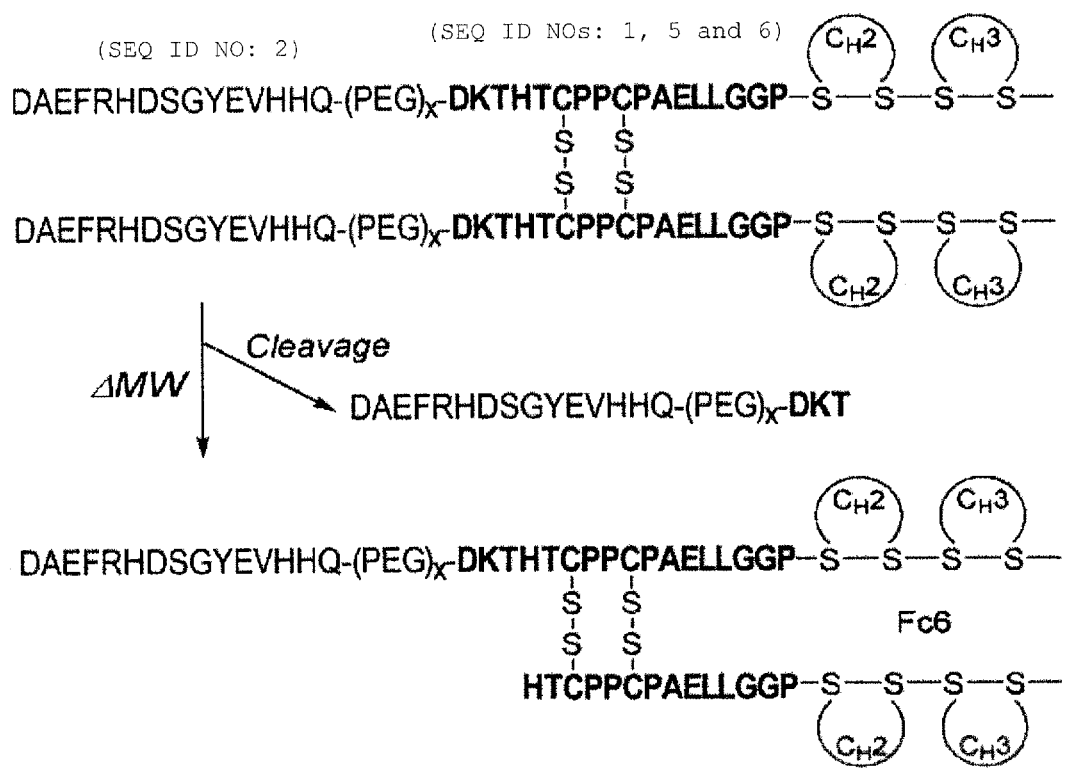
FIG. 11 is a schematic diagram of the structures of two-handed and one-handed Aβ-PEG$_x$-Fc fusion proteins showing a model for the generation of a one-handed fusion protein heterodimer by cleavage of a two-handed fusion protein homodimer, wherein the sequences of the IgG1 hinge region are indicated by boldface.

DKTHT = SEQ ID NO: 1
DAEFRHDSGYEVHHQ = SEQ ID NO: 2 molecular weight of the fragment Aβ-PEG$_x$-DKT. These results strongly suggest that the smaller chain present in the one-handed heterodimer is not the expected unreacted Fc6 monomer chain but instead represents the Aβ-PEG$_x$-Fc reaction product which has been subsequently cleaved between the $^{223}$Thr residue and the $^{224}$His residue within the upper hinge region (DKTHT (SEQ ID No. 1)) (FIG. 11).

(Surface Plasmon Resonance Tests)

As the major reaction product obtained for all the four Aβ symmetroadhesins was the two-handed homodimer, the present inventors investigated whether such preparations had the ability to bind to dimeric targets as two-handed molecules. This analysis was carried out using a monoclonal antibody capable of interacting with both of the Aβ sequences that were incorporated into the two-handed symmetroadhesin homodimers. The DAEFRHDSGYEVHHQ sequence (SEQ ID No. 2) is well suited for this purpose as the sequence contains the principal epitope (EFRHD (SEQ ID No. 3)) recognized by some monoclonal antibodies that are reactive with human Aβ (1-42) fibrils including 6E10[18], PFA1 and PFA2[19], WO2[20], and 12A11, 10D5, and 12H4[21]. Accordingly, the present inventors characterized the binding of the Aβ symmetroadhesins of the present inventors to one of these antibodies (6E10) using surface plasmon resonance (SPR). The present inventors compared the binding of Aβ peptides containing the DAEFRHDSGYEVHHQ sequence (SEQ ID No. 2) which were expected to bind to 6E10 in a one-handed manner. FIGS. 12 to 14 show the results obtained when 6E10 was immobilized on the surface of the SPR chip. Specific binding was observed with all the four Aβ symmetroadhesins (FIGS. 12A, 12B, 13A, and 13B) and with two Aβ peptides, i.e., pen-Aβ and Aβ-pra (Table 1) (FIGS. 14E and 14F), that Table 4 shows the kinetic results of Mab-6E10 binding measured by surface plasmon resonance.

The kinetic binding curves for both of the Aβ peptides gave a good fit with a 1:1 Langmuir model ($x^2<0.1$) which was consistent with one-handed binding. In contrast, the four Aβ symmetroadhesins did not give a good fit with the 1:1 Langmuir model ($x^2>10$), and this indicated two classes of binding sites. As shown in Table 4, a good fit was obtained for the four Aβ symmetroadhesins by employing a two-exponential model ($x^2<1.1$) The single affinity site exhibited by the pen-Aβ (17 nM) and Aβ-pra (20 nM) peptides was similar to the low affinity sites observed for the Aβ-Fc (140 nM), Aβ-PEG$_{12}$-Fc (93 nM), Aβ-PEG$_{24}$-Fc (70 nM), and Aβ-PEG$_{36}$-Fc (62 nM) symmetroadhesins (Table 4). This affinity site was consistent with a one-handed binding mechanism by a fraction of the symmetroadhesin population. In addition, the A62 -Fc, Aβ-PEG$_{12}$-Fc, Aβ-PEG$_{24}$-Fc and Aβ-PEG$_{36}$-Fc symmetroadhesins all exhibited a much higher affinity site that was greater by two to five orders of magnitude over the corresponding low affinity sites, and this provided strong evidence for the existence of two-handed binding of 6E10 by a significant fraction (19-27%) of the Aβ symmetroadhesins (Table 4).

[Discussion]

Proteins prefer to form compact globular or fibrous structures, so that their exposure to solvent is minimized. This tendency is inherent both in the polypeptide backbone having a propensity for hydrogen-bound secondary structure, and in side chain interactions that promote tertiary folding. Therefore, most of previous efforts to introduce "flexibility" into antibodies using peptides have been inadequate. For example, it is common to employ a combination of an amino acid that favors solvent interactions (e.g., serine) and an amino acid that breaks a helical structure (e.g., glycine). This approach is useful in making fusion proteins such as single-chain antibody fragments (scFv), but the resulting structures are quite compact with no evidence of extendibility (for example, see Reference Document 20). Further, such sequences are likely to cause additional problems due to their intrinsic immunogenicity and proteolytic susceptibility.

The present inventors pursued a novel strategy that introduces a nonprotein chain into the hinge region by chemical semisynthesis. The results of the present inventors demonstrate quantitative yields of antibody-like molecules having nonprotein hinge parts that connect the two $A\beta_{1-15}$ peptides with the Fc dimer. These molecules form two-handed native dimers that exhibit high affinity for an anti-A$\beta$ monoclonal antibody. The A$\beta$-PEG$_x$-Fc dimer having a nonprotein hinge part of the present inventors has an affinity that is two to five orders of magnitude greater than the cognate peptide, and is therefore considered to bind much better than the A$\beta$-Fc dimer. The full interpretation of these results awaits the determination of three-dimensional structure of the $A\beta_{1-15}$ peptide, which contains the immunodominant epitope of Alzheimer's A$\beta$(1-42) fibrils. The exact configuration of this epitope (DAEFRHDS (SEQ ID No. 10)) in complex with the Fab fragments has been resolved in X-ray structures[19),21)], but the same region appears disordered in 3D structures of A$\beta$(1-42) fibrils obtained by quenched hydrogen/deuterium exchange NMR studies[27)].

The analysis by SDS-polyacrylamide gel electrophoresis indicates that the formation of the desired A$\beta$-PEG$_x$-Fc fusion protein exceeds 90%. In addition, the MS analysis of the one-handed reaction products purified by SEC indicates that they contain two reacted Fc polypeptides (FIG. 11), one of which is full-length but the other of which has been hydrolyzed at the T/HT sequence that is a major site of proteolysis (e.g., papain)[9)]. Therefore, the overall efficiency of the native chemical ligation step, excluding the subsequent cleavage, may be much closer to 100%. The native ligation conditions also appear to be completely compatible with the native structure and bioactivity of the Fc dimer, while imparting some of the properties of nonprotein polymers. The results of the present inventors indicate that the addition of discrete oxyethylene oligomers not only improves binding but also appears to have a significant effect on the hydrodynamic radius of the Fc protein as evidenced by the size exclusion chromatography of the A$\beta$-PEG$_{12}$-Fc, A$\beta$-PEG$_{24}$-Fc, and A$\beta$-PEG$_{36}$-Fc molecules when compared with the A$\beta$-Fc molecule.

MALDI-TOF MS appears to be ideally suited for the characterization of the novel protein-nonprotein-protein molecules of the present inventors. The most part contributed by the hybrid structures can be efficiently characterized not only in tryptic digests, but also in the two-handed and one-handed native Fc dimers. Ionization and desorption appear to be mediated by the adjacent protein sequences in the protein-nonprotein hybrid molecules of the present inventors, and this suggest the application of this approach to a broad range of chemically distinct polymer chains.

In conclusion, the present inventors have described here a significant step toward the goal of the present inventors, i.e., toward the complete chemical semisynthesis of antibodies having nonprotein hinge parts that incorporate large binding domains such as the Fab region itself or receptor extracellular domains. Additional progress will depend upon the identification of other protein ligation reactions that can be combined with a native chemical ligation; that are similarly compatible with the native structure and function of the cognate proteins; and that can efficiently proceed at micromolar concentrations that are achievable using such native proteins in solution. The antibody-like molecule that is envisioned by the present inventors has enormous potential as a candidate therapeutic agent having improved binding affinity for disease targets.

REFERENCE DOCUMENTS (1) Pauling, L. (1940) A theory of the structure and process of formation of antibodies. J. Am. Chem. Soc. 62, 2643-2657.
(2) Porter, R. R. (1958) Separation and isolation of fractions of rabbit gamma-globulin containing the antibody and antigenic combining sites. Nature 182, 670-671.
(3) Edelman, G. M., Cunningham, B. A., Gall, W. E., Gottlieb, P. D., Rutishauser, U. and Waxdal, M. J. (1969) The covalent structure of an entire .Gimmunoglobulin molecule. Proc. Natl. Acad. Sci. U.S.A. 63, 78-85.
(4) Feinstein, A. and Rowe, A. J. (1965) Molecular mechanism of formation of an antigen-antibody complex. Nature 205, 147-149.
(5) Valentine, R. C. and Green, N. M. (1967) Electron microscopy of an antibody hapten complex. J. Mol. Biol. 27, 615-617.
(6) Saphire, E. O., Stanfield, R. L., Crispin, M. D., Parren, P. W., Rudd, P. M., Dwek, R. A., Burton, D. R. and Wilson, I. A. (2002) Contrasting IgG structures reveal extreme asymmetry and flexibility. J. Mol. Biol. 319, 9-18.
(7) Capon, D. J., Chamow, S. M., Mordenti, J., Marsters, S. A., Gregory, T., Mitsuya, H., Byrn, R. A., Lucas, C., Wurm, F. M., Groopman, J. E., Broder, S. and Smith, D. H. (1989) Designing CD4 immunoadhesins for AIDS therapy. Nature 337, 525-531.
(8) Byrn, R. A., Mordenti, J., Lucas, C., Smith, D., Marsters, S. A., Johnson, J. S., Cossum, P., Chamow, S. M., Wurm, F. M., Gregory, T., Groopman, J. E. and Capon, D. J. (1990) Biological properties of a CD4 immunoadhesin. Nature 344, 667-670.
(9) Chamow, S. M., Peers, D. H., Byrn, R. A., Mulkerrin, M. G., Harris, R. J., Wang, W. C., Bjorkman, P. J., Capon, D. J. and Ashkenazi, A. (1990) Enzymatic cleavage of a CD4 immunoadhesin generates crystallizable, biologically active Fd-like fragments. Biochemistry 29, 9885-9891.
(10) Ward, R. H., Capon, D. J., Jett, C. M., Murthy, K. K., Mordenti, J., Lucas, C., Frie, S. W. Prince, A. M., Green, J. D. and Eichberg, J. W. (1991) Prevention of HIV-1 IIIB infection in chimpanzees by CD4 immunoadhesin. Nature 352, 434-436.
(11) Watson, S. R., Imai, Y. , Fennie, C., Geoffrey, J. S., Rosen, S. D. and Lasky, L. A. (1990) A homing receptor-IgG chimera as a probe for adhesive ligands of lymph node high endothelial venules. J. Cell Biol. 110, 2221-2229.
(12) Watson, S. R., Fennie, C. and Lasky, L. A. (1991) Neutrophil influx into an inflammatory site inhibited by a soluble homing receptor-IgG chimaera. Nature 349, 164-167.
(13) Ashkenazi, A., Marsters, S. A., Capon, D. J., Chamow, S. M., Figari, I. S., Pennica, D., Goeddel, D. V., Palladino, M. A. and Smith, D. H. (1991) Protection against endotoxic shock by a tumor necrosis factor receptor immunoadhesin. Proc. Natl. Acad. Sci. U.S.A. 88, 10535-10539.
(14) Ashkenazi, A., Capon, D. J. and Ward, R. H. (1993) Immunoadhesins. Int. Rev. Immunol. 10, 219-227.

(15) Reichert, J. M. (2011) Antibody-based therapeutics to watch in 2011. MAbs 3, 76-99.
(16) Flory, P. J. (1969) Statistical Mechanics of Chain Molecuries. Interscience Publishers, New York.
(17) Dawson, P. E. and Kent, S. B. (2000) Synthesis of native proteins by chemical ligation. Annu. Rev. Biochem. 69, 923-960.
(18) Pirttila, T., Kim, K. S., Mehta, P. D., Frey, H. and Wisniewski, H. M. (1994) Soluble amyloid Oprotein in the cerebraspinal fluid from patients with Alzheimer's disease, vascular dementia and controls. J. Neural. Sci. 127, 90-95.
(19) Gardberg, A. S., Dice, L. T., Ou, S., Rich, R. L., Helmbrecht, E., Ko, J., Wetzel, R., Myszka, D. G., Patterson, P. H. and Dealwis, C. (2007) Molecular basis for passive immunotherapy of Alzheimer's disease. Proc. Natl. Acad. Sci. U.S.A. 104, 15659-15664.
(20) Robert, R., Dolezal, O., Waddington, L., Hattarki, M. K., Cappai, R., Masters, C. L., Hudson, P. J. and Wark, K. L. (2009) Engineered antibody intervention strategies for Alzheimer's disease and related dementias by targeting amyloid and toxic oligomers. Protein Eng. Des. Sel. 22, 199-208.
(21) Basi, G. S., Feinberg, H., Oshidari, F., Anderson, J., Barbour, R., Baker, J., Comery, T. A., Diep, L., Gill, D., Johnson-Wood, K., Goel, A., Grantcharova, K., Lee, M., Li, J., Partridge, A., Griswold-Prenner, I., Piot, N., Walker, D., Widom, A., Pangalos, M. N., Seubert, P., Jacobsen, J. S., Schenk, D. and Weis, W. I. (2010) Structural correlates of antibodies associated with acute reversal of AO-related behavioral deficits in a mouse model of Alzheimer disease. J. Biol. Chem. 285, 3417-3427.
(22) Tanaka, K., Waki, H., Ido, Y., Akita, S., Yoshida, Y. and Yoshida, T. (1988) Protein and polymer analyses up to m/z 100,000 by laser ionization time-of-flight mass spectrometry. Rapid Commun. Mass Spectrom. 2, 151-153.
(23) Koy, C., Mikkat, S., Raptakis, E., Sutton, C., Resch, M., Tanaka, K. and Glocker, M. O. (2003) Matrixassisted laser desorption/ionization-quadrupole ion trap-time of flight mass spectrometry sequencing resolves structures of unidentified peptides obtained by in-gel tryptic digestion of haptoglobin derivatives from human plasma proteomes. Proteomics 3, 851-858.
(24) Kabat, E. A., Wu, T. T., Perry, H. M., Gottesman, K. S. and Foeller, C. (1991) Sequences of Proteins of Immunological Interest, 5th ed. National Institutes of Health, Bethesda, Md.
(25) Rajendra, Y., Kiseljak, D., Baldi, L., Hacker, D. L. and Wurm, F. M. (2011) A simple high-yielding process for transient gene expression in CHO cells. J. Biotechnol. 153, 22-26
(26) Johnson, E. C. and Kent, S. B. (2006) Insights into the mechanism and catalysis of the native chemical ligation reaction. J. Am. Chem. Soc. 128, 6640-6646.
(27) Luhrs, T., Ritter, C., Adrian, M., Riek-Loher, D., Bohrmann, B., Dobeli, H., Schubert, D. and Riek, R. (2005) 3D structure of Alzheimer's Aβ(1-42) fibrils. Proc. Natl. Acad. Sci. U.S.A. 102, 17342-17347.

The invention claimed is:

1. A flexible molecule having a nonpeptide hinge part, comprising a molecular recognition system-forming substance X, an alkyleneoxide-containing group Y bound to the molecular recognition system-forming substance X, an antibody upper hinge region-forming sequence $Z_U$ bound to the alkyleneoxide-containing group Y, and an antibody Fc fragment comprising, at its N-terminal side, an antibody core hinge region-forming sequence $Z_C$ bound directly to the C-terminal side of the antibody upper hinge region-forming sequence $Z_U$, wherein:
  a) the molecular recognition system-forming substance X is
    (i) a peptide composed of 2 to 50 amino acid residues, or
    (ii) an antibody Fab fragment,
    and is capable of non-covalent binding with a target molecule;
  b) the alkyleneoxide-containing group Y is a polyalkyleneglycol group, the polymerization degree of which is from 2 up to 36;
  c) the antibody core hinge region-forming sequence $Z_C$ consists of the sequence CPPC (SEQ ID No. 5); and
  d) the antibody upper hinge region-forming sequence $Z_U$ comprises 3 to 5 amino acids, the sequence of which is or is within, the sequence of the IgG1 upper hinge region, DKTHT (SEQ ID No. 1).

2. The flexible molecule according to claim 1 wherein the polyalkyleneglycol group is formed by polymerization of an alkyleneglycol group of 2 to 6 carbon atoms.

3. The flexible molecule according to claim 1 wherein the polyalkyleneglycol group is a polyethyleneglycol group or polypropyleneglycol group.

4. The flexible molecule according to claim 1 wherein the polymerization degree of the polyalkyleneglycol group is from 12 up to 36.

5. The flexible molecule according to claim 1 wherein the alkyleneoxide-containing group is a polyethyleneglycol group, the polymerization degree of which is from 12 up to 36.

6. The flexible molecule according to claim 1, comprising two nonpeptide hinge part-containing groups each containing the molecular recognition system-forming substance X, the alkyleneoxide-containing group Y, and the antibody core hinge region-forming sequence $Z_C$ bound directly to the C-terminal side of the antibody upper hinge region-forming sequence $Z_U$, wherein the antibody Fc fragment is present in a dimer.

7. The flexible molecule according to claim 6 wherein the polyalkyleneglycol group is formed by polymerization of an alkyleneglycol group of 2 to 6 carbon atoms.

8. The flexible molecule according to claim 6 wherein the polyalkyleneglycol group is a polyethyleneglycol group or polypropyleneglycol group.

9. The flexible molecule according to claim 6 wherein the polymerization degree of the polyalkyleneglycol group is from 12 up to 36.

10. The flexible molecule according to claim 6 wherein the alkyleneoxide-containing group is a polyethyleneglycol group, the polymerization degree of which is from 12 up to 36.

11. A method for producing a flexible molecule having a nonpeptide hinge part, the method comprising:
  a) preparing a nonpeptide hinge part-containing thioester (XYZ$_U$-COSR) containing a molecular recognition system-forming substance X, an alkyleneoxide-containing group Y, and an antibody upper hinge region-forming sequence $Z_U$, wherein:
    i) the molecular recognition system-forming substance X represents a peptide composed of 2 to 50 amino acid residues or an antibody Fab fragment and is capable of non-covalent binding with a target molecule,
    ii) the alkyleneoxide-containing group Y represents a polyalkyleneglycol group, the polymerization degree of which is from 2 up to 50,
    iii) the antibody upper hinge region-forming sequence $Z_U$ comprises 3 to 5 amino acids of the sequence of the IgG1 upper hinge region, DKTHT (SEQ ID No. 1),
    iv) COSR represents a thioester group of the C-terminal amino acid residue of the antibody upper hinge region-forming sequence $Z_U$, and
    v) R represents an organic group;
  b) preparing a peptide containing an antibody Fc fragment, the peptide having an antibody Fc fragment and an N-terminal cysteine residue;
  c) subjecting the nonpeptide hinge part-containing thioester (XYZ$_U$-COSR) and the peptide containing an antibody Fc fragment to a native chemical ligation under non-denaturing, reducing conditions to obtain a molecule which comprises a XYZ$_U$-group and an antibody Fc fragment bound to the XYZ$_U$-group via the cysteine residue.

12. The flexible molecule according to claim 1 wherein the polymerization degree of the polyalkyleneglycol group is 12.

13. The flexible molecule according to claim 1 wherein the polyalkyleneglycol group is a polyethyleneglycol group, the polymerization degree of which is 12.

14. The flexible molecule according to claim 6 wherein the polymerization degree of the polyalkyleneglycol group is 12.

15. The flexible molecule according to claim 6 wherein the polyalkyleneglycol group is a polyethyleneglycol group, the polymerization degree of which is 12.

16. The method of claim 11, wherein the Fc fragment comprises, at its N-terminal side, an antibody core hinge region-forming sequence $Z_C$ bound directly to the C-terminal side of the antibody upper hinge region-forming sequence $Z_U$, wherein the antibody core hinge region-forming sequence $Z_C$ consists of the sequence CPPC (SEQ ID No. 5).

17. The method of claim 11, wherein the polymerization degree of the polyalkyleneglycol group is from 2 up to 36.

18. The method of claim 11, wherein the polymerization degree of the polyalkyleneglycol group is from 12 up to 36.

* * * * *